United States Patent [19]

Santa et al.

[11] 3,991,040

[45] Nov. 9, 1976

[54] AROMATIC IMIDODICARBOXYLIC ACID DIALLYL ESTERS, PREPOLYMERS THEREOF, CURED RESINS THEREOF, AND PROCESSES FOR PRODUCING THESE

[75] Inventors: Toshihiro Santa; Yuzo Aito, both of Hino; Katsuhisa Watanabe, Hino; Kiyokazu Tsunawaki, Hachioji; Yuji Mitani, Hino; Kiyoshi Nawata, Hachioji, all of Japan

[73] Assignee: Teijin Limited, Osaka, Japan

[22] Filed: Mar. 26, 1975

[21] Appl. No.: 562,093

Related U.S. Application Data

[62] Division of Ser. No. 393,839, Sept. 4, 1973, Pat. No. 3,931,224.

[30] Foreign Application Priority Data

| Sept. 7, 1972 | Japan | 47-89104 |
| Sept. 8, 1972 | Japan | 47-89536 |
| Dec. 22, 1972 | Japan | 47-129127 |
| Dec. 22, 1972 | Japan | 47-129128 |

[52] U.S. Cl. ............ 260/79.3 R; 260/32.6 N; 260/37 N; 260/37 P; 260/47 UA; 260/78.41; 260/78.5 UA; 260/326 C; 260/326 A; 260/326 N; 260/326 S; 526/82; 526/266

[51] Int. Cl.² ............ C08F 18/16; C08F 28/00; C08F 218/16; C08G 75/22

[58] Field of Search ....... 260/326 A, 326 C, 47 UA, 260/79.3 R, 78.4 A, 78.5 UA, 88.3 R

[56] References Cited

UNITED STATES PATENTS 3,217,014  11/1965  VanStrien et al. ............ 260/326 A

*Primary Examiner*—Ronald W. Griffin
*Attorney, Agent, or Firm*—Sherman & Shalloway

[57] ABSTRACT

New curable monomeric aromatic imidodicarboxylic acid diallyl esters, such as 4-allyloxycarbonyl-N-(allyloxycarbonylmethyl)phthalimide, 1,2-ethylene bis(4-allyloxycarbonylphthalimide), or N,N'-bis(allyloxycarbonylmethyl) pyromellitimide. When heated in the presence of a free radical initiator, these monomers give cured polymers having very superior mechanical strength, thermal stability, chemical resistance and electrical properties. If this polymerization is stopped before the reaction mixture is gelled, prepolymers can be obtained. The cured polymers are especially useful as electronics materials and engineering plastics.

6 Claims, No Drawings

AROMATIC IMIDODICARBOXYLIC ACID DIALLYL ESTERS, PREPOLYMERS THEREOF, CURED RESINS THEREOF, AND PROCESSES FOR PRODUCING THESE

This is a division of application Ser. No. 393,839, filed Sept. 4, 1973, now U.S. Pat. No. 3,931,224, issued Jan. 6, 1976.

This invention relates to curable monomeric aromatic imidodicarboxylic acid diallyl esters, prepolymers thereof, cured resins thereof, and to processes for producing these.

It is an object of this invention to provide novel aromatic imidodicarboxylic acid diallyl esters capable of forming novel diallyl-type cured resins containing an aromatic imide group, prepolymers thereof, and processes for producing these.

Another object of this invention is to provide novel aromatic diallyl imidodicarboxylates which when heated in the presence of a free radical initiator, easily polymerize to polymers useful as industrial material of very superior mechanical strength, thermal stability, chemical resistance and electrical properties; prepolymers thereof; and curable compositions containing these; and also processes for producing said diallyl esters, said prepolymers, and said polymers.

Conventional diallyl-type cured resins include, for example, diallyl ortho-phthalate resin (DAP resin), and diallyl isophthalate resin (DAIP resin). Generally, these resins have good thermal stability, electrical characteristics, mechanical properties, and chemical resistance, and there has been an increasing demand for these resins in many applications. However, the DAP and DAIP resins cannot meet the requirements of shapability and thermal stability which have recently become more severe. For example, in the thermal stability classification of electrical insulating materials, the DAP resin is classified as Class B (130° C.) and the DAIP resin, as Class F (155° C.), but no diallyl-type cured resins having greater thermal stability have ever been developed.

Furthermore, the DAIP resin, especially its prepolymer, has poor storage stability, and has not gained widespread acceptance.

According to the present invention, there are provided cured resins having superior electrical and mechanical characteristics and chemical resistance and especially superior thermal stability as compared with the conventional DAP resin or DAIP resin; monomeric aromatic diallyl imidodicarboxylates capable of forming such cured resins; prepolymers of said diallyl esters; and processes for producing these.

The invention will be described in detail below with reference to the monomeric aromatic diallyl imidodicarboxylates and a process for their preparation; prepolymers derived from the monomeric diallyl esters, and a process for their preparation; and a curable composition comprising said monomeric diallyl esters, said prepolymers, or a mixture of these, and a process for preparing said cured resins from this composition.

Aromatic Diallyl Imidodicarboxylates (monomer) and Process for Preparation Thereof

(I-1) Monomers used in this invention

The novel aromatic imidodicarboxylic acid diallyl ester (monomer) of this invention is expressed by the following formula (1)

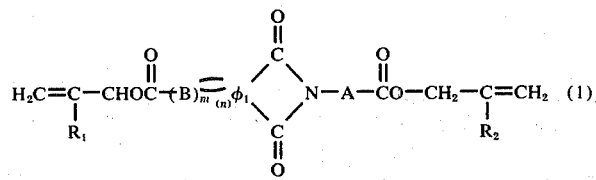

wherein $R_1$ and $R_2$ are the same or different and represent a hydrogen atom or methyl group; $\phi_1$ is a trivalent or tetravalent aromatic group expressed by the following formula,

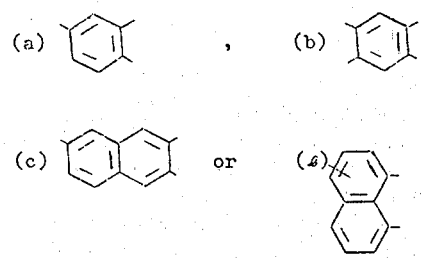

(l) represents an m- or p-oriented bond,

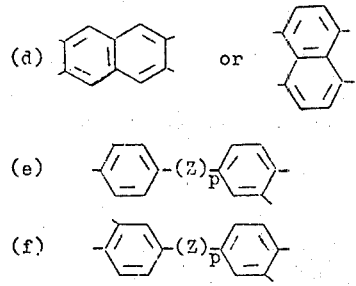

$p$ in the formula (e) and (f) representing 0 or 1, and when $p$ is 0, the two benzene rings are directly bonded to each other, and when $p$ is 1, Z is $-SO_2-$, $-O-$, or a divalent lower hydrocarbon residue; m and n each represent 0 or 1, when one of $m$ or $n$ is 0, the other is also 0, and in this case, the allyloxy carbonyl group of the formula

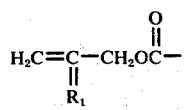

is directly bonded to $\phi_1$, and when $m$ and $n$ are both 1,

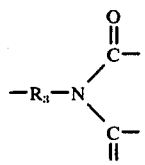

represents the following formula

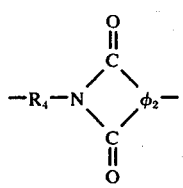

wherein $R_3$ is a divalent aliphatic, alicyclic, or aromatic organic radical; and A represents the following formula $$-R_4-$$

or

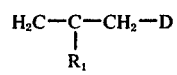

wherein $R_4$ is a divalent aliphatic, alicyclic, or aromatic organic radical and is the same as or different from $R_3$, and $\phi_2$ represents a trivalent aromatic group (a), (c) or (e), $\phi_2$ and $\phi_1$ being the same or different.

The aromatic imidodicarboxylic acid diallyl esters of this invention expressed by formula (1) can be produced, for example, by reacting an aromatic imidodicarboxylic acid expressed by the formula (2)

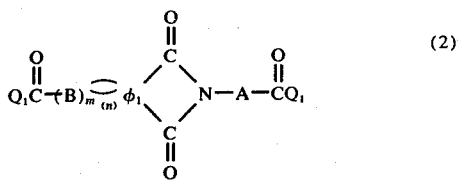

wherein B, $m$, $n$, $\phi_1$ and A are the same as defined with respect to formula (1), and $Q_1$ is a halogen atom, or —OM, in which M is a hydrogen atom, a lower alkyl group, alkali metal or alkaline earth metal, or its functional derivative with at least 2 molar times the amount of said compound of a reactive allyl compound expressed by formula (3)

$$H_2C=C-CH_2-D \quad (3)$$
$$\phantom{H_2C=}|$$
$$\phantom{H_2C=}R_1$$

wherein $R_1$ is a hydrogen atom or methyl group, D is a hydroxyl group when $Q_1$ is a halogen atom, or a halogen atom when $Q_1$ is —OM and M is an alkali metal or alkaline earth metal, and when $Q_1$ is a hydroxyl group or lower alkoxy group, D is either a halogen atom or a hydroxyl group.

The aromatic nucleus of $\phi_1$ the aromatic radical in formula (a) to (f) which constitutes the above aromatic imidodicarboxylic acid diallyl ester may be replaced by a substituent for example, a halogen atom such as chlorine, bromine or iodine, a lower alkyl group, or lower alkoxy group.

The formula (1) expressing the aromatic imidodicarboxylic acid diallyl ester (monomer) of this invention can be shown by the following formulae (1-A) and (1-B).

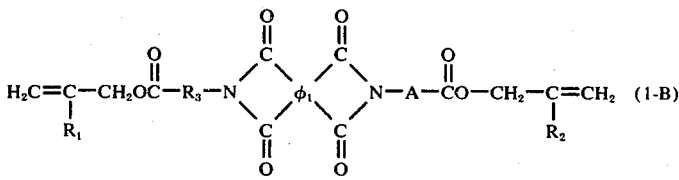

wherein $R_1$, $R_2$, $\phi_1$ and A are the same as in formula (1).

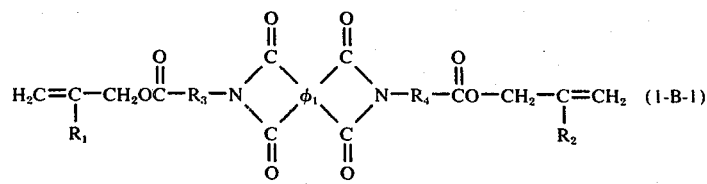

wherein $R_1$, $R_2$, $R_3$ $\phi_1$ and A are the same as defined in formula (1).

Of the aromatic imidodicarboxylic diallyl esters of formula (1-B), those expressed by formula (1-B-1)

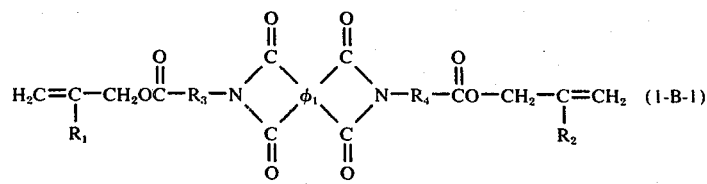

and the aromatic imidodicarboxylic acid allyl ester of formula (1-A) are preferred because they are relatively easy to synthesize and give cured resins having superior thermal stability and electrical characteristics.

Especially, the compounds of the following formula (1-A-1), (1-A-2) and (1-B-2)

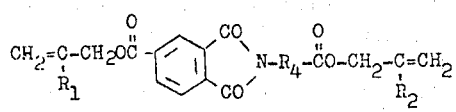

(1-A-1)

wherein $R_1$, $R_2$ and $R_3$ are the same as in formula (1)

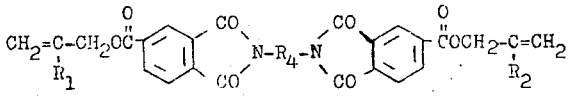

(1-A-2)

wherein $R_1$, $R_2$ and $R_4$ are the same as in formula (1)

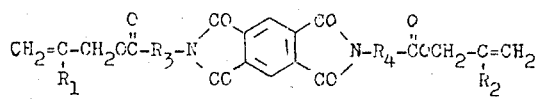

(1-B-2)

wherein $R_1$, $R_2$, $R_3$ and $R_4$ are the same as in Formula (1) are very preferred monomers since they are easy to synthesize and give cured resins having excellent physical properties, especially excellent thermal stability and electrical characteristics.

The benzene ring in the above formulae (1-A-1), (1-A-2) and (1-B-2) may be replaced by a substituent, for example, a halogen atom such as chlorine bromine or iodine, a lower alkyl group, or a lower alkoxy group.

(I-2) Process for Preparation of the Monomers

As already described, the monomers expressed by the formula (1) are prepared by reacting the aromatic imidodicarboxylic acid of formula (2) or its functional derivative with the reactive allyl compound of formula (3). This reaction is the so-called esterification reaction, and can be preformed under any esterification conditions known to those skilled in the art.

The monomers expressed by the formula (1-A-1) can be prepared by reacting the aromatic imidodicarboxylic acid of formula (2) or its functional derivative of formula (2-1)

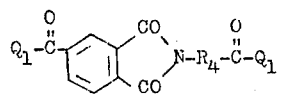

(2-1)

wherein $Q_1$ and $R_4$ are the same as defined with respect to formula (2),
with the reactive allyl compound of formula (3).

Likewise, the monomers of formula (1-A-2) and (1-B-2) can be prepared by reacting a compound of formula (2-2)

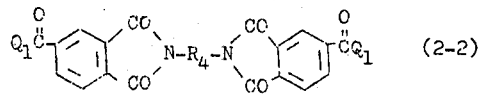

(2-2)

and a compound of formula (2-3)

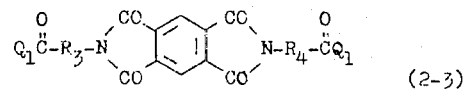

(2-3)

wherein $R_3$, $R_4$ and $Q_1$ are the same as defined with respect to formula (2), respectively with the reactive allyl compound of formula (3).

Preferred examples of $Q_1$ in the formulae (2), (2-1), (2—2) and (2-3) are halogen atoms such as chlorine, bromine or iodine, or -OM groups in which M is a hydrogen atom, a lower alkyl group such as a methyl, ethyl or propyl group, an alkali metal such as sodium, potassium or lithium, or an alkaline earth metal such as calcium or barium.

Whilst the process for producing the aromatic imidodicarboxylic acid diallyl esters of this invention has been described above with reference to the case in which $\phi_1$ and $\phi_2$ are benzene rings in formula (2), it should be understood that these monomers can be prepared equally easily by reacting the aromatic imidocarboxylic acid of formula (c), (d), (e) or (f) given above with the reactive allyl compound of formula (3).

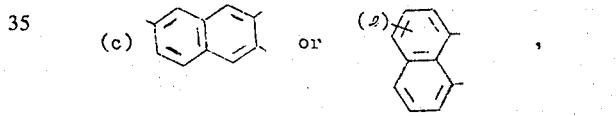

(l) represents an m- or p-oriented bond,

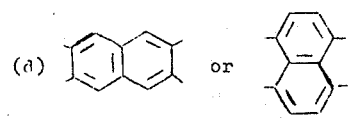

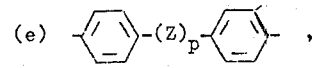

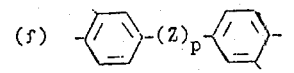

wherein Z and P are the same as in formula (1).

In the above formula (2), (2-1), (2-2) and (2-3), $R_3$ and $R_4$ are the same or different, and each represent a divalent aliphatic, alicyclic or aromatic organic radical.

Examples of $R_3$ and $R_4$ are as follows:

a. Aliphatic radicals having 1 to 20 carbon atoms, such as a methylene, ethylene, trimethylene, tetramethylene, hexamethylene, octamethylene, nonamethylene, decamethylene, or dodecamethylene group, b. Alicyclic radicals having 6 to 20 carbon atoms, such as a cyclohexylene group or

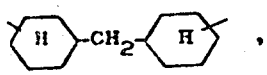

c. Aromatic radicals having 6 to 20 carbon atoms, such as a p-phenylene group, m-phenylene group, p-xylylene group, m-xylylene group, biphenylene group,

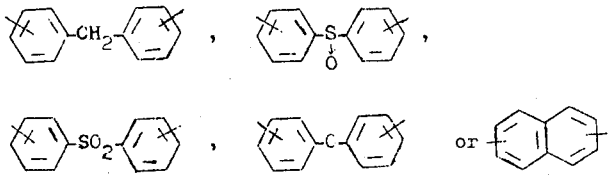

The divalent organic radical represented by $R_3$ and $R_4$ may be replaced by a substituent, for example, a halogen atom such as chlorine, bromine or iodine, a lower alkyl group, or a lower alkoxy group.

Aromatic imidodicarboxylic acids of formulae (2), (2—1), (2—2), and (2—3) wherein M is a hydrogen atom can be easily prepared, for example, by reacting an aromatic tricarboxylic monohydride (for example, trimellitic anhydride) with an aminocarboxylic acid or diamine, or by reacting an aromatic tetracarboxylic dianhydride (for example, pyromellitic anhydride) with an aminocarboxylic acid.

The aminocarboxylic acid and the diamine are compounds having an active amino group. Specific examples are:

Aminocarboxylic acid

Aliphatic aminocarboxylic acids having 1 to 20 carbon atoms such as glycine, alanine, valine, leucine, iso-leucine, phenylalanine, β-aminopropionic acid, γ-aminobutyric acid or anthranilic acid, ε-aminocaproic acid; alicyclic aminocarboxylic acids having 6 to 20 carbon atoms such as 2-aminocyclohexanecarboxylic acid, 3-aminocyclohexanecarboxylic acid, or 4-aminocyclohexanecarboxylic acid; and aromatic aminocarboxylic acids having 6 to 20 carbon atoms such as m-aminobenzoic acid, p-aminobenzoic acid, 4,4'-aminodiphenylcarboxylic acid, 5-amino-naphthoic acid-1, or 7-amino-naphthoic acid-2.

Diamines

Aliphatic diamines having 1 to 20 carbon atoms such as ethylene diamine, trimethylene diamine, tetramethylene diamine, hexamethylene diamine, octamethylene diamine, nonamethylene diamine, decamethylene diamine or dodecamethylene diamine; alicyclic diamines having 6 to 20 carbon atoms such as diaminocyclohexane, bis(4-aminocyclohexane), or bis(4-aminocyclohexyl)methane; and aromatic diamines such as p-phenylene diamine, m-phenylene diamine, p-xylylene diamine, m-xylylene diamine, benzidine, 3,3'- or 4,4'-diaminediphenyl methane, 3,3'- or 4,4'-diaminodiphenyl sulfoxide, 3,3'- or 4,4'-diaminodiphenyl sulfone, 3,3'- or 4,4'-diaminodiphenyl ether, or diaminonaphthalene.

Furthermore, by reacting the above aromatic imidodicarboxylic acid with a halogenating agent such as a thionyl halide, phosphorus trihalide, or phosphorus pentahalide, compounds of the above general formulae in which $Q_1$ is a halogen atom are obtained. Further, by reacting them with metal alcoholates alkali hydroxides, or alkaline earth metal compounds, compounds in which $Q_1$ is OM in which M is an alkali metal or alkaline earth metal are obtained easily. Further reaction of these with lower alcohols yields compounds in which $Q_1$ is OM with M representing a lower alkyl group.

Specific examples of the reactive allyl compound of formula (3) for producing the monomers of this invention include allyl alcohol, methyllyl alcohol, allyl chloride, allyl bromide, allyl iodide, methallyl chloride, methallyl iodide, and methallyl bromide.

Preferred reactions for preparing the monomers of this invention from the aromatic imidodicarboxylic acids of formula (2) or the functional derivatives thereof and the reactive allyl compounds of formula (3) include, for example, (1) a reaction between a diimidocarboxylic acid or its lower alkyl ester and allyl alcohol, (2) a reaction between a diimidodicarboxylic acid halide and allyl alcohol, or (3) a reaction between a diimidodicarboxylic acid or its metal salt and an allyl halide.

The reaction (1) is performed by mixing a diimidodicarboxylic acid with 1 to 30 equivalents, preferably 5 to 20 equivalents, based on the dimidodicarboxylic acid, of allyl alcohol, adding a small amount of an esterification catalyst such as sulfuric acid, hydrochloric acid or p-toluenesulfonic acid, and if desired adding a substance which forms an azeotrope with water, such as benzene, toluene or xylene, in order to remove water from the reaction system. The reaction temperature differs according to the type of the diimidodicarboxylic acid, but is generally 60° to 220° C., preferably 80° to 200° C. After the reaction, the product is washed with water, and then distilled or recrystallized from a solvent to form the intended diallyl ester.

The reaction (2) is performed by heating in the presence of a dehydrohalogenation agent. Preferred dehydrohalogenation agents are basic substances such as triethyl amine, dimethyl aniline, pyridine or magnesium.

The reaction (3) is advantageous from the viewpoint of the starting materials. The reaction can be completed by converting the diimidodicarboxylic acid substantially to its metal salt, and heating it in solvent or an allyl halide. The diimidodicarboxylic acid need not always be isolated in the form of metal salt, but can be offered for the reaction in the form of a mixture with an equivalent of an alkaline compound such as sodium carbonate, potassium carbonate, sodium hydrogen carbonate, or potassium hydrogen carbonate.

Examples of the solvent are aromatic solvents such as o-xylene, toluene, nitrobenzene, or N,N-dimethylaniline; polar aprotic solvents such as dimethyl formamide, dimethyl sulfoxide, tetramethylurea, tetramethylene sulfone, N-methyl pyrrolidone or hexamethyl phosphoramide; glycols such as ethylene glycol, diethylene glycol or triethylene glycol; and glycol ethers such as ethylene glycol monomethyl ether, ethylene glycol dimethyl ether, or triethylene glycol monoethylene ether. These are used either alone or in admixture. Depending upon the type of the solvent and the type of the diimidodicarboxylic acid, the reaction can be accelerated by using a catalyst.

Examples of such a catalyst include metal halides such as potassium iodide, sodium iodide, copper iodide, potassium bromide or sodium bromide; ammonium halides such as ammonium bromide or ammonium iodide; tertiary amines such as trimethyl amine or triethyl amine; quaternary ammonium salts such as tetramethyl ammonium chloride, or benzyl trimethyl ammonium bromide; and halogens such as bromide or iodine.

The reaction can be performed by dispersing or dissolving the diimidodicarboxylic acid metal salt in the solvent and gradually adding dropwise at least 2 molar times, based on the metal salt, of an allyl halide while maintaining the reaction temperature at 60° to 200° C., preferably 80° to 180° C. The amount of the solvent is not particularly limited, but for ease of stirring, heat transmission, and dissolution, the preferred amount is at least 2 times the weight of the dicarboxylic acid metal salt.

After the reaction, the by-products such as metal halides are separated by filtration, and the solvent is removed. Then, the product is distilled or recrystallized from a suitable solvent to form the intended diallyl ester in good yield.

The preferred methods for producing the monomers of this invention have been described above. It should be understood that the monomers of this invention may be those which are produced by any other methods.

[I-3] Examples of the Monomers

Preferred examples of the monomers of this invention will be shown below. It is to be noted that these examples are given in order to facilitate the understanding of the monomers of this invention, and they are not intended to limit the monomers of this invention.

1. Monomers of formula (1-A-1)
No. 1: 4-Allyloxycarbonyl-N-(allyloxycarbonylmethyl) phthalimide

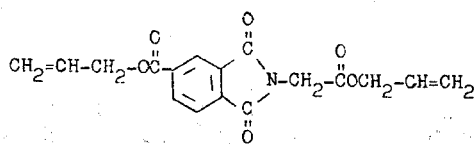

No. 2: 4-Allyloxycarbonyl-N-(allyloxycarbonylpentamethyl) phthalimide

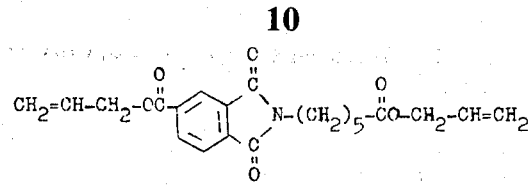

No. 3: 4-Allyloxycarbonyl-N-(4-allyloxycarbonylcyclohexyl) phthalimide

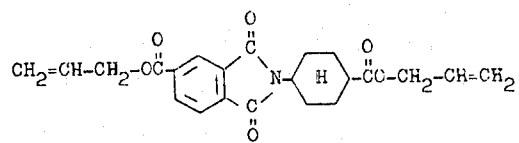

No. 4: 4-Allyloxycarbonyl-N-(4-allyloxycarbonylphenyl) phthalimide

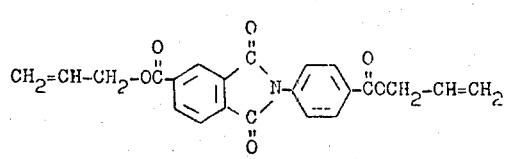

No. 5: 4-Allyloxycarbonyl-N-(4,4'-allyloxycarbonyldiphenyl) phthalimide

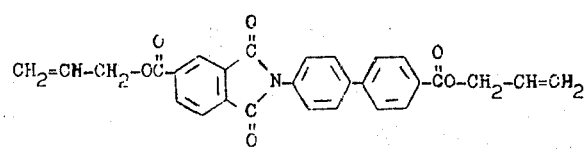

No. 6: 4-Allyloxycarbonyl-N-(3-allyloxycarbonylphenyl) phthalimide

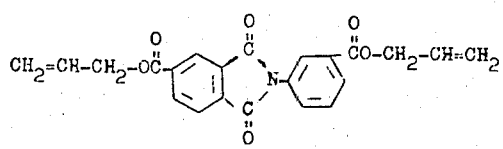

2. Monomers of formula (1-A-2)
No. 7: 1,2-Ethylene bis(4-allyloxycarbonylphthalimide)

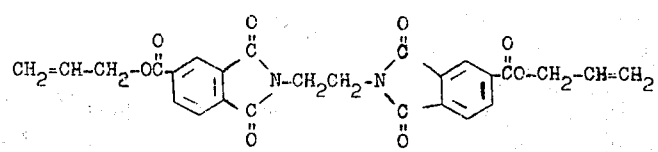

No. 8: 1,6-Hexamethylene bis(4-allyloxycarbonylphthalimide)

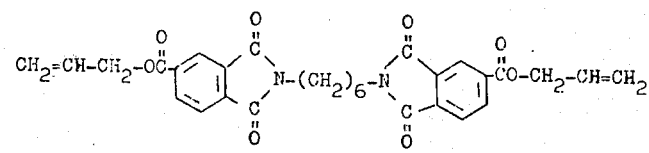

No. 9: 1,12-Dodecamethylene bis(4-allyloxycarbonylphthalimide)

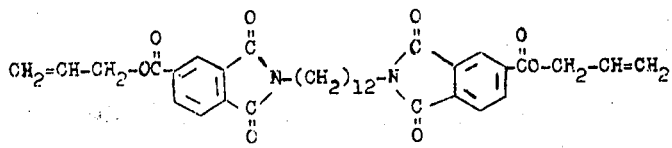

No. 10: 1,4-Cyclohexylene bis(4-allyloxycarbonylphthalimide)

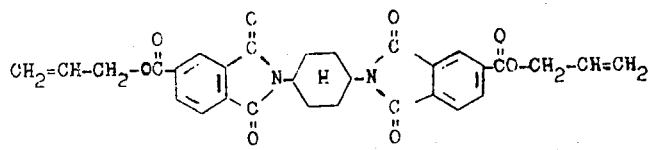

No. 11: 4,4'-Dicyclohexylmethane bis(4-allyloxycarbonylphthalimide)

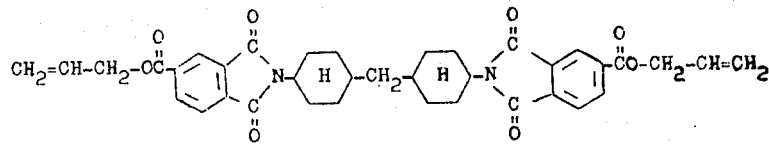

No. 12: Methaphenylene bis(4-allyloxycarbonylphthalimide)

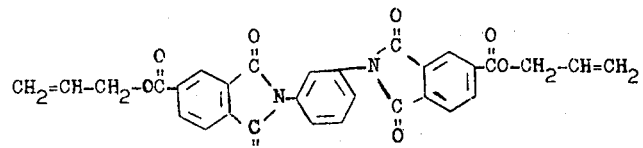

No. 13: Paraphenylene bis(4-allyloxycarbonylphthalimide)

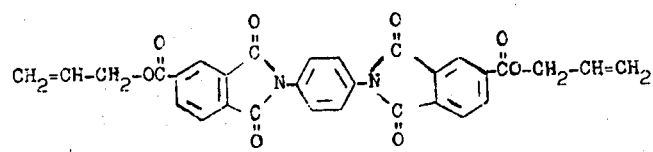

No. 14: 4,4'-Diphenylsulfoxide bis(4-allyloxycarbonylphthalimide)

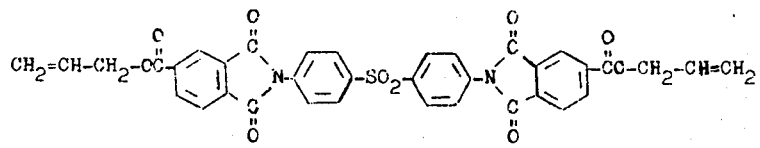

No. 15: 4,4'-Diphenylether bis(4-allyloxycarbonylphthalimide)

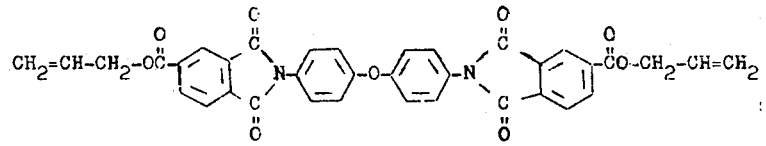

No. 16: 1,5-Naphthalene bis(4-allyloxycarbonylphthalimide)

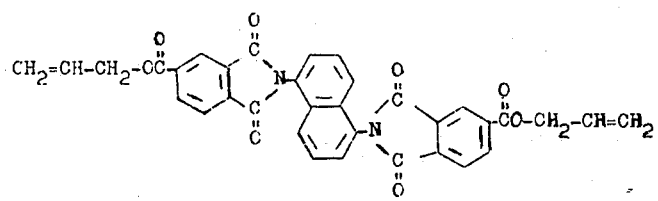

3. Monomers of formula (1-B-2):
No. 17: N,N′-bis(allyloxycarbonylmethyl)pyromellitimide No. 21: N,N′-bis(3-allyloxycarbonylphenyl)pyromellitimide

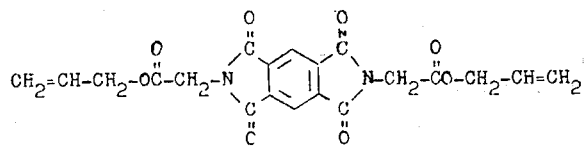

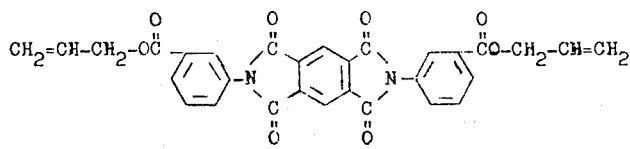

No. 18: N,N′-bis(allyloxycarbonylpentamethyl)-pyromellitimide

No. 22: N,N′-bis(4-allyloxycarbonyl)pyromellitimide

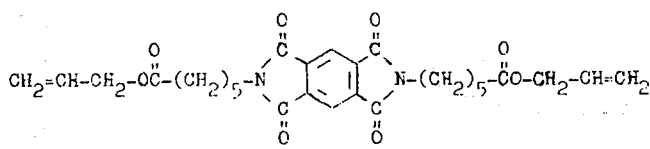

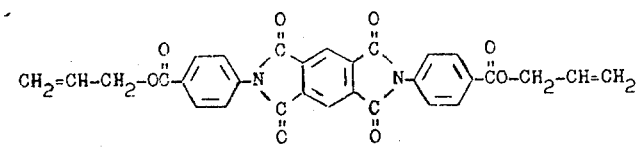

No. 19: N,N′-bis(3-allyloxycarbonylcyclohexyl)-pyromellitimide

4. Monomers not belonging to (1) – (3):
No. 23: N,N′-bis(allyloxycarbonylmethyl)-3,3′,4,4′-diphenylsulfonetetracarbodiimide

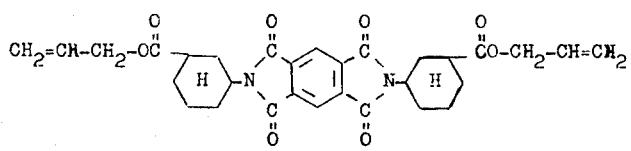

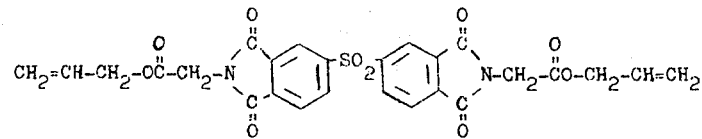

No. 20: N,N′-bis(4-allyloxycarbonylcyclohexyl)-pyromellitimide

No. 24: N,N′-bis(allyloxycarbonylpentamethyl)-3,3′,4,4′-diphenylsulfonetetracarbodiimide

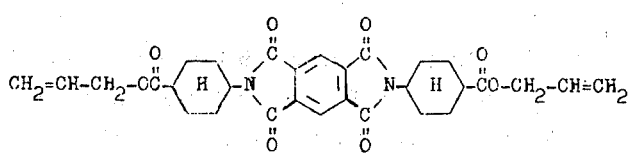

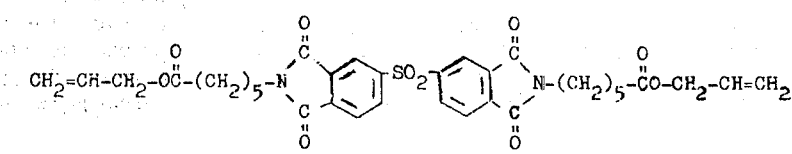

No. 25: N,N'-bis(3-allyloxycarbonylphenyl)-3,3',4,4'-diphenylsulfonetetracarbodiimide

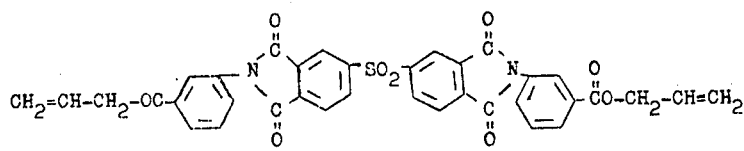

No. 26: N,N'-bis(4-allyloxycarbonylphenyl)-3,3',4,4'-diphenylsulfonetetracarbodiimide

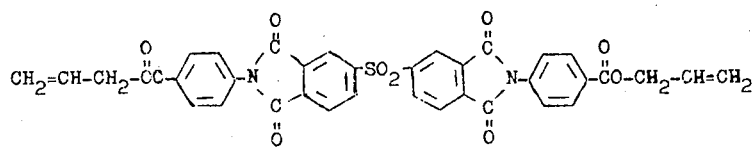

No. 27: N,N'-bis(allyloxycarbonylmethyl)-1,4,5,8-naphthalenetetracarbodiimide

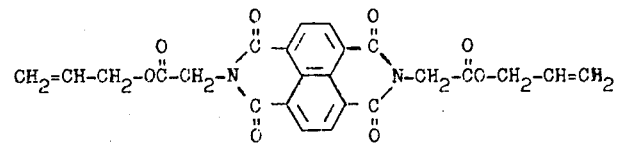

No. 28: N,N'-bis(allyloxycarbonylpentamethyl)-1,4,5,8-naphthalenetetracarbodiimide

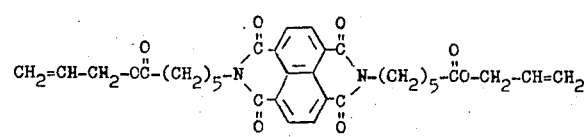

No. 29: N,N'-bis(3-allyloxycarbonylcyclohexyl)-1,4,5,8-naphthalenetetracarbodiimide

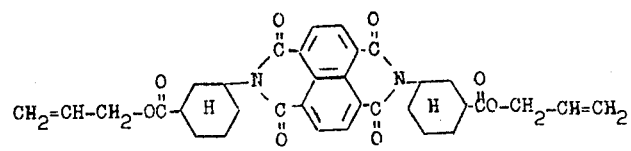

No. 30: N,N'-bis(3-allyloxycarbonylphenyl)-1,4,5,8-naphthalenetetracarbodiimide

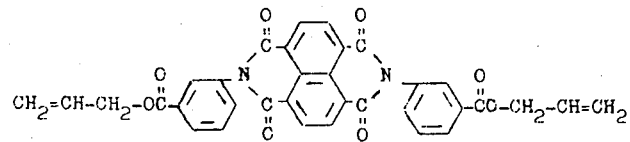

No. 31: N,N'-bis(4-allyloxycarbonylphenyl)-1,4,5,8-naphthalenetetracarbodiimide

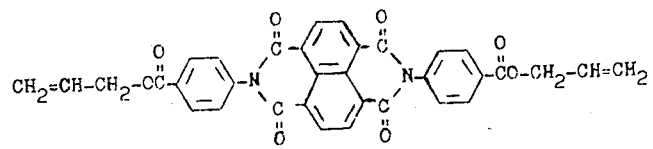

(II) Prepolymers and Process for Preparation Thereof (II-1) Process for Preparing Prepolymers According to this invention, at least one of the monomers of the formula (1), (1-A) or (1-B) is prepolymerized to form a substantially linear prepolymer. The prepolymerization may be performed by heating preferably in the presence of a free radical initiator. Accordingly, the curable prepolymer of this invention can be prepared by heating at least one of the monomers of formula (1), namely the aromatic diallyl imidodicarboxylate, in the presence of a free radical initiator to polymerize the diallyl ester, stopping the polymerization reaction before the reaction mixture is gelled, and if desired, separating and recovering the polymeric product.

Accordingly, if the monomer of formula (1-A-1), (1-A-2), or (1-B-2) is used in the above method, the corresponding curable prepolymer can be prepared.

The prepolymer of this invention has in its molecule unsaturated bonds ascribable to the allyl residue, and is soluble in solvent. It also has thermoplasticity.

The preferred method for preparing such a prepolymer of this invention comprises heating the monomer of formula (1) either as such or as diluted with a solvent, preferably in the presence of a free radical initiator and in the presence or absence of a gas containing oxygen, and stopping the reaction before the gellation of the reaction mixture takes place, usually when about 5 to 9% of the monomer is converted to a prepolymer.

Various solvents can be used to dilute the monomer, and specific examples include aliphatic alcohols having 3 to 5 carbon atoms, aromatic hydrocarbons such as benzene, toluene, xylene, ethylbenzene, cumene or hexylbenzene, lower aliphatic ketones such as acetone, methyl ethyl ketone or methyl isobutyl ketone, lower saturated or unsaturated aliphatic aldehydes or derivatives thereof, such as acetaldehyde, paraacetaldehyde, propionaldehyde, n-butyraldehyde or crotonaldehyde, benzyl-type compounds such as benzyl alcohol, methylbenzyl alcohol, dimethylbenzyl alcohol, chlorobenzyl alcohol or dimethylbenzyl chloride, substituted aromatic compounds such as chlorobenzene, cinnamyl alcohol, cyanobenzene or tetrahydronaphthalene, and carbon tetrachloride.

According to the proportion of the diluent used, not only is it possible to control the temperature of the reaction system, but also it is possible to control the rate of polymerization or the molecular weightof the polymer.

The free radical initiator may, for example, be organic peroxides such as caprylyl peroxide, lauroyl peroxide, benzoyl peroxide, t-butyl peracetate, t-butyl perbenzoate, dicumyl peroxide, t-butylhydroperoxide, methyl ethyl ketone peroxide, di-butyl peroxide or cumene hydroperoxide, azo compounds such as 2,2'-abobisisobutyronitrile, gases containing oxygen, and many other equivalently effective substances. The suitable amount of the initiator is usually 0.05 to 5% by weight based on the monomer used. The initiator may be added at the initiation of polymerization, or continuously added at the initial stage of polymerization. It may be used in bulk or as diluted in the solvent or monomer.

Various additives can be used in the polymerization according to this invention. Specifically, organic metal compounds or radical capturing agents may be added before or during polymerization in order to control the rate of polymerization, the molecular weight of the polymer, or the molecular weight distribution, inhibit side-reactions (cyclization, branching, etc.), prevent the gellation of the polymer, or modify the resulting polymer.

Especially useful additives includes organo-tin compounds such as tetrabutyl tin, dibutyl tin dichloride, dibutyl tin dibromide, dibutyl tin chloride acetate, dibutyl tin diacetate, dibutyl tin oxalate, dibutyl tin dilaurate, tin diphenolate, triethyl tin chloride, tripropyl tin bromide, triphenyl tin chloride, tribenzyl tin chloride, 1,3,5-tris (tributyl tin) hexahydrotriazine-2,4,6-trione, bistributyl tin oxide, dibutyl tin oxide, dipropyl tin sulfide, dioctyl tin oxide, or tribenzyl tin hydroxide, organo-lead compounds such as tetraethyl lead, tetraphenyl lead, trimethyl lead chloride, tri-n-propyl lead chloride, or triphenyl lead hydroxide, organo-germanium compounds such as tetraethyl germanium, tetraphenyl germanium, triethyl bromogermanium, di-n-propyl dichlorogermanium, methyl triiodogermanium, or hexamethyl digermanium; as radical capturing agents, quinones such as p-benzoquinone, chloranil, anthraquinone or phenanthroquinone, aromatic polyhydroxy compounds such as p-tertiary butyl catechol, hydroquinone, resorcinol, or catechol, aromatic nitro compounds such as m-dinitrobenzene, 2,4-dinitrotoluene or trinitrophenol, aromatic nitron compounds such as nitronbenzene or nitron-3-naphthol, aromatic amino compounds such as methyl aniline, p-phenylene diamine, or N,N'-tetraethyl-p-phenylene diamine, and organic sulfur compounds such as tetramethyl thiuram disulfide, dithiobenzoyl disulfide, p,p'-ditolyl trisulfide, and p,p'-ditolyltetrasulfide.

The amount of the additive is 0.05 to 5% by weight based on the monomer, in the case of the organo-metal compound, and 0.01 to 1% by weight based on the monomer in the case of the radical capturing agent.

In the preparation of the prepolymer, a part (preferably not more than 40 mol%, especially not more than 30 mol%) of the diallyl ester expressed by the above general formula may be replaced by another copolymerizable compound having an unsaturated bond.

Examples of the compound having an unsaturated bond are vinyl monomers such as acrylonitrile, styrene, methyl methacrylate or maleic anhydride; diallyl esters or dimethally esters of dibasic acids such as orthophthalic acid, iso-phthalic acid, terephthalic acid, hexahydro-orthophthalic acid, hexahydro-iso-phthalic acid, hexahydro-terephthalic acid, methylphthalic acid, methylisophthalic acid, methylterephthalic acid, diphenyldicarboxylic acid, diphenylmethanedicarboxylic acid, diphenylether dicarboxylic acid, diphenylsulfonedicarboxylic acid, naphthalenedicarboxylic acid, maleic acid, fumaric acid, adipic acid, muconic acid, dimethylmuconic acid or HET acid; monoallyl esters of monobasic acids, such as allyl benzoate, allyl methacrylate or allyl naphthoate; and polyallyl esters such as triallyl trimellitate, triallyl cyanurate, triallyl isocyanurate, triallyl phosphate or pentaerythritol tetrakis allyl phthalate.

If the amount of the copolymerizable compound having an unsaturated bond in the precopolymer is too large, it is difficult to produce a cured resin having superior thermal stability. Accordingly, it is advantageous to adjust the amount to not more than 40 mol%, especially less than 30 mol%, more preferably less than 20 mol%, based on the monomer used for preparing the prepolymer.

In the polymerization reaction in accordance with the present invention, the reaction temperature can be varied over a wide range according to the presence, type or amount of the free radical initiator, diluent or additives. Generally, it is preferred that the temperature should be 60° to 250° C. Especially when an organic peroxide is used as the free radical initiator, it is convenient to use an organic solvent to adjust the reflux temperature, and operate under total reflux at a temperature of 75° to 200° C. In this reaction, pressures over a wide range can be used, but generally, it is preferred that the reaction be carried out at atmospheric pressure.

The time required to complete the reaction is affected by various conditions. The reaction is stopped by lowering the temperature before the occurrence of gellation, or by diluting the reaction mixture in an inert substance, or by adding a polymerization inhibitor. The decomposition of the converted prepolymer is performed, for example, by mixing it with a medium which dissolves the monomer but not the prepolymer and extracting and separating the unreacted monomer and if desired, also the polymerization solent or additives.

(II-2) Prepolymer

The prepolymer of this invention so produced is substantially linear and solvent soluble, and has thermoplasticity.

The prepolymer of this invention is a prepolymer in which at least 60 mol%, preferably at least 70 mol%, above all at least 80 mol%, of the total recurring units are composed of recurring units of the formula (4)

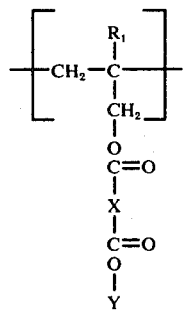

(4)

wherein Y is an allyl group of the formula $$-CH_2C=CH_2 ;$$
$$\phantom{-CH_2C=}|$$
$$\phantom{-CH_2C=}R_2$$

$R_1$ and $R_2$ are the same or different and represent e hydrogen atom or methyl group; and X is a trivalent or tetravalent aromatic radical expressed by the formula

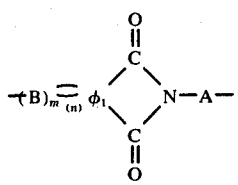

in which $\phi_1$ is

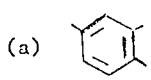 , 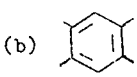

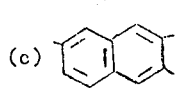 or 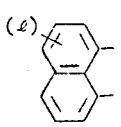

($\ell$) showing on m- or p-oriented bond,

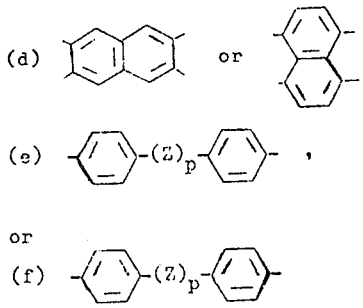

$p$ in the formulae (e) and (f) represents 0 or 1, when $p$ is 0, the two benzene rings are directly bonded, and when $p$ is 1, Z in —$SO_2$—, —O— or a divalent lower hydrocarbon residue; $m$ and $n$ are 0 or 1, when one of $m$ and $n$ is 0, the other is also 0, and in this case the allyloxy carbonyl group expressed by the formula $$H_2C=C-CH_2OC-$$
$$\phantom{H_2C=}|\phantom{CH_2O}\|$$
$$\phantom{H_2C=}R_1\phantom{CH_2}O$$

is directly bonded to $\phi_1$, and when $n$ and $m$ are both 1,

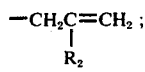

represents the following formula $$\phantom{-R_3-N}\!\!\!\overset{O}{\underset{\phantom{|}}{\|}}$$
$$\phantom{-R_3-N}\!\!\!C-$$
$$-R_3-N$$
$$\phantom{-R_3-N}\!\!\!C-$$
$$\phantom{-R_3-N}\!\!\!\underset{\phantom{|}}{\overset{\|}{O}}$$

wherein $R_3$ is a divalent aliphatic, alicyclic or or aromatic organic radical, andA is an atomic group of the following formula $$-R_4-$$

or $$-R_4-N\diagdown\!\!\diagup\phi_2-$$

(with C=O groups forming a ring)

wherein $R_4$ is a divalent aliphatic, alicyclic or aromatic organic radical and are the same a or different from $R_3$, and $\phi_2$ is a trivalent aromatic radical of formula (a), (c) or (e), $\phi_2$ and $\phi_1$ being the same or different, with the proviso
that X is bonded to

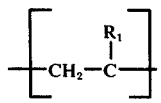

through

either via A or B, This prepolymer has a relative viscosity [$\eta_{rel.}$], as measured at 30°C. on a solution of 1.0 g of the prepolymer in 100 ml. of N,N-dimethyl formamide as a reference solvent, of 1.05 to 1.35, preferably 1.05 to 1.25.

Furthermore, by using a diallyl ester of a dibasic acid copolymerizable with the monomer of this invention during manufacture, the prepolymer of this invention can contain recurring units of the following formula (5)

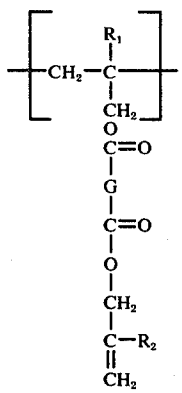

wherein $R_1$ and $R_2$ are the same or different and each represent a hydrogen atom or methyl group, and G is a divalent aliphatic, alicyclic or aromatic hydrocarbon radical having 1 to 12 carbon atoms, in an amount not in excess of 40 mol%, preferably not in excess of 30 mol%, of the total recurring units of the prepolymer. The prepolymers of the formulae (4) and (5) and suitably have a molecular weight of 300 to 1100, preferably 300 to 900, most preferably 300 to 650, per double bond (polymerizable double bond) of the allyl group contained therein.

Those prepolymers having a number average molecular weight of about 2,000 to 30,000, especially 2,500 to 20,000, are preferred because their flowability is suitable for fabrication.

The prepolymers are solid thermoplastic polymers having a residual unsaturated bond, and when further polymerized, can be converted to heat-infusible crosslinked thermosetting resins which are insoluble in organic solvents.

[III] Process for Producingg Curable Composition and Cured Resins

According to this invention, a cured resin can be prepared by maintaining a. an aromatic imidodicarboxylic acid diallyl ester (monomer) of the formula (1), b. a curable prepolymer having a relative viscosity, measured by the method described hereinabove, of 1.05 to 1.35, preferably 1.05 to 1.25 in which at least 60 mol%, preferably at least 70 mol% of the total recurring units are composed of recurring units of the formula (4), or c. A mixture of the diallyl ester (a) above with the prepolymer (b) above, under suitable polymerization conditions.

The curable prepolymer (b) above may be a coprepolymer consisting of not more than 40%, preferably not more than 30 mol%, based on the total recurring units, of the recurring units of the formula (5) above, and at least 60 mol%, preferably at least 70 mol% of recurring units of formula (4).

Likewise, there can be used a mixture of at least 60 mol%, preferably at least 70 mol%, of an aromatic imidodicarboxylic acid diallyl ester of the formula (1) above with not more than 40 mol%, preferably not more than 30 mol%, of a diallyl dicarboxylate expressed by the formula (6)

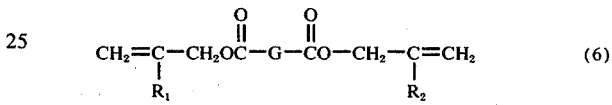

wherein $R_1$ and $R_2$ are the same or different and represent a hydrogen atom or methyl group, and G is a divalent aliphatic, alicyclic or aromatic hydrocarbon radical having 2 to 12 carbon atoms.

As already stated, a part or whole of the dicarboxylic acid diallyl ester of formula (6) may be replaced by another unsaturated compound copolymerizable with the monomer of the formula (1). Or the prepolymer may be one in which not more than 40 mol%, preferably not more than 30 mol%, based on the total recurring units, of such a copolymerizable unsaturated compound is copolymerized with the monomer of the formula (1). If the proportion of the copolymerizable component is large, the physical properties, especially thermal stability, of the resulting cured resin are deteriorated. Accordingly, it is preferred that the proportion of the copolymerizable component should not exceed 20 mol%. Such a copolymerizable component has already been described under the headline prepolymer.

The above monomer or prepolymer or a mixture of these can be converted to a cured resin by heating, or applying ionizing radiation or electron beams. The resulting cured resin is a heat-infusible, organic solvent-insoluble hard resin in which the molecules are aligned three-dimensionally.

When the curing is performed by heating, it is effective to add a suitable amount of a polymerization initiator, for example, an organic peroxide such as di-tertbutyl peroxide, tert.-butyl hydroperoxide, tert.-butyl perbenzoate, benzoyl peroxide, dicumyl peroxide, or cumene hydroperoxide, tert.butyl peroxylaurate, cyclohexanone peroxide, methyl ethyl ketone peroxide, tert.-butyl cumyl peroxide, diisopropyl benzene hydroperoxide, 2,5-dimethyl hexane, 2,5-dihydroperoxide. The amount of the initiator is preferably 0.3 to 5% by weight per 100 parts by weight of the above monomer, prepolymer or mixture of these.

The heat curing can be performed by heating to 100° to 200°C. for 0.5 min. to 10 hrs.

The heat curing in the presence of a polymerization initiator is most recommended for curing, but the use of electron beams for the curing is also effective. The monomer or prepolymer can be easily polymerized by irradiating electron beams in a dose of about 0.5 to 70 Mrad. For example, when it is to be polymerized on the surface of a substrate, the use of electron beams gives a cured film within very shot periods of time.

When the polymerization is carried out using light, it is preferred to use the organic peroxide together with a light sensitizer.

In curing of the monomer, prepolymer or mixture, a pigment, internal mold releasng agent, polymerization promotor, polymerization retardant, stabilizer, or an inorganic or organic filler may be added in an amount such as not impair the effects of the present invention, in order to improve the shapability, storability and other properties of the cured resin.

Examples of the inorganic filler are mica, asbestos, glass powder, silica, clay "SHIRASU" (white volcanic ash accumulated in Kagoshima Prefecture, Japan), titanium oxide, magnesium, oxide, alumina, asbestos fibers, silica fibers, glass fibers, silicate glass fibers, alumina fibers, carbon fibers, boron fibers, beryllium fibers, steel fibers, and whiskers.

Examples of the organic filler include polyethylene, polypropylene, polyvinyl chloride, polyvinyl fluoride, poly (methyl methacrylate), polybutadiene, aliphatic and aromatic polyamides, imide polymers, ester imide polymers, amide imide polymers, pulp, acrylic fibers, polyester fibers such as polyethylene terephthalate fibers, cotton, and rayon.

The suitable amount of such a filler is usually up to 500 parts by weight per 100 parts of the resin component.

Since the properties of the filler affect the properties of the cured product, the choice of the type and amount of it must be made having regard to the properties of the intended cured products. Where the cured product especially requires thermal stability, the inorganic filler or organic fillers having superior thermal stability, such as polyvinyl fluoride, polybutadiene, aromatic polyamides, amide imide polymers or imide polymers, must be selected.

The internal mold releasing agent may be a longchain aliphatic carboxylic acid such as stearic acid or lauric acid, or its metal salt.

The polymerization promotor is effective for increasng the rate of polymerization, or lowering the polymerization temperature. Examples are organic cobalt compounds such as cobalt naphthenate or cobalt octylate.

The polymerization retarding agent is effective for controlling the rate of polymerization to form uniform cured products, and hydroquinone, n-propyl gallate, p-benzoquinone, tetramethyl thiuram disulfide, or methoquinone is used, for example.

The mixing of these fillers and other additives can be made easy by adding an organic solvent.

Examples of such a solent include aromatic hydrocarbons such as benzene or toluene, ketones such as acetone or methyl ethyl ketone, esters such as ethyl acetate, ethers such as ethyl ether, or ethylene glycol monomethyl ether, alcohols such as methanol or ethanol, and halogenated hydrocarbons such as chloroform or methylene chloride, or dimethylformamide and N-methyl pyrrolidone.

The processes of the present invention are applicable, for example, to the following methods.

1. A casting method in which the resin is placed in a mold and polymerized and cured.
2. An injection molding or transfer molding method which comprises heating the resin to render it flowable, feeding it to a heated mold, and polymerizing and curing it.
3. A compression molding method involving heating the resin under pressure in a mold thereby to cure it.
4. A method of forming a laminate, which comprises dissolving the resin in an organic solvent, impregnating a fibrous sheet such as a non-woven cloth or glass matt with the resulting solution, drying it to remove the solvent, and then polymerizing the resin in the fibrous sheet.
5. A coating method in which a resin solution or a fine powdery resin is coated on a substrate and polymerized on the substrate.
6. A method of forming a decorative plate which comprises impregnating a resin solution into a printing paper for example, precuring the resin to drive off the solvent, and then heating the precured resin under pressure on a substrate.

The cured resins so obtained have extremely superior thermal stability, electrical characteristics, mechanical characteristics, and chemical resistance, especially the thermal stability and storage stability, which are not seen in the conventional cured resins, and have a wide range of utility. Especially useful applications are found in electronics materials which require light weight and compact size and high levels of thermal stability and electrical characteristics, and engineering plastics.

Properties of the hardened resins and propolymers of this invention were measured in accordance with the method mentioned below.

1. Heat Distortion Temperature:

Column-shaped test pieces of a size 125 mm long, 6.0 mm thick and 12.8 mm wide were prepared from a hardened resin, and were placed on the support rack with the distance between the support points being 10.0 cm apart. The support rack was immersed in the silicon oil at 20°C, and the load F (Kg) calculated by the equation $$F = \frac{2Sbd^2}{3l}$$

in which S is a maximum fiber stress of the test pieces (18.5 Kg/cm$^2$), $b$ is a thickness of the test piece (cm), $d$ is the width of the test piece (cm), and e is the distance (10 cm) between the support points. was applied to the center midway between the support points. Then the bath was heated at a rate of 2°C/min, and the temperature at which the deflection of the test piece has reached 0.25 mm was read to determine the heat distortion temperature of the hardened resin, in accordance with ASTM 648-45T.

2. Borcol Hardness:

Hardness was measured using Impressor (No. 934-1) made by Barber-Colman Co.

3. Flexural Strength and Flexural Modulus:

A test piece of the same shape as used in the above-mentioned heat distortion temperature measurement was placed on the support rack with the distance between the support points being 100 mm. Load at a rate of 5 mm/min was applied to the center between the support points through a wedge having a roundness of 5 mm, to read the load until the test piece is broken. Flexural strenth $\sigma_f$ (Kg/mm$^2$) and flexural modulus $E_f$(Kg/mm$^2$) were calculated from the following equations $$\sigma_f = \frac{3\,Pl}{2\,bd^2}$$

$$E_f = \frac{l^3 m}{4\,bd^3}$$

in which P is the load (Kg) when the test piece has broken, e is the distance (100 mm) between the support points, b is the width of the test piece (mm), d is the thickness of the test piece (mm) and m is a gradient (Kg/mm) of tangent at the initial straight line part of the curve of load vs. deflection.

The above method accords with ASTM-D-790.

4. Volume Resistivity:

A disc-shaped hardened resin test piece of a size of 50 mm in diameter and 3 mm in thickness was prepared and treaed in boiling water for 2 hours. By using a megger made by Toa Denpa Co., the voltage of DC 500 volts was applied to examine the elecctric resistance as one-minute value (resistance after one minute of voltage application). This method accords with ASTM-D-257.

5. Arc-Resistance:

Tungsten electrodes, 6.35 mm spaced apart, were held on a test piece of the same shape as that used in 4) above, — angle between the electrode axis and the test piece surface being 35° – and applied with an open voltage of 12500 volts. By measuring the time (in second) until the arcing is extinguished, the arc-resistance was determined. This method accords with ASTM-D-495.

6. Dielectric Constant ($\epsilon$) and Dissipation factor (tan $\sigma$):

A disc-shaped hardened resin test piece of a size of 50 mm in diameter and 3 mm in thickness was prepared, both of which surfaces was coated with a metal foil as a main electrode and counter electrode. Measurement was made by "Mutual Bridge Method" with a frequency of 1 × 10$^3$ Hz.

7. Weight Loss on Heating:

Measured by thermal gravimetry. This is, by using a thermobalance measuring instrument manufactured by Rigaku Denki Co., the weight loss on heating at a rate of 5° C/min in air was examined. The temperature at which the weight loss has started or the temperature at which 5% of the weight has lost, was based on a criterion of evaluating the heat resistance.

8. Heat Deterioration Testing:

Hardened resin test pieces were held in an air oven heated at 260° C for 10, 100, and 1000 hours. Weight loss rate and flexural strength holding rate during such heat treatments were measured to evaluate heat resistance.

9. Resistance to Chemicals:

Hardened resin test pieces were boil-treated in an aqueous solution of 10% caustic soda and an aqueous solution of 10% sulfuric acid, for 50 and 100 hours. Barcol hardness holding rate of the test pieces were measured to determine resistance to chemicals.

10. Relative Viscosity ($\eta$rel) of the Prepolymer:

One gram of prepolymer was dissolved in 100 ml of N,N-dimethylformamide, and by using Ubbelohde type viscometer, the flow down time (t sec) at 30.0° C. of the resulting solution was compared to the flow down time ($t_0$ sec) of said solvent, to determine the relative viscosity in terms of the ratio $t/t_0$.

11. Preservation Stability of the Prepolymer:

The prepolymer was hold in an air oven set at 100° C for 20 hours, and the distance the plunger has lowered down (mm/min) was measured by flow tester (Shimazu Mfg. Co.).

| | |
|---|---|
| Plunger | 10 mm in diameter |
| Load | 100 Kg/cm$^2$ |
| Nozzle | 1 mm in diameter, 1 mm length |
| Temperature | 100° C. |
| Preheating | 2 minutes |

*See "Kogyo Zairyo" (Industrial Material), Vol. 18, No. 10, p. 164, 1970.

EXAMPLE

Part I (Synthesis of aromatic imide dicarboxylic acid diallyl ester)

I-a Synthesis of 4-allyloxycarbonyl-N-(4-allyloxycarbonylphenyl) phthalimide of the above-mentioned formula No. 4 i. 71.0 Parts of the above white powdery imidedicarboxylic acid disodium salt was prepared by taking 62.2 parts of 4-hydroxycarbonyl-N-(4-hydroxycarbonylphenyl)phthalimide of the formula

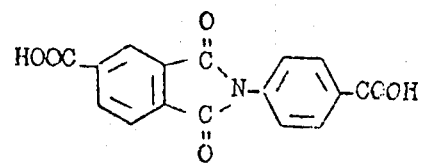

into an aqueous solution containing 16.2 parts of sodium hydroxide, and the mixture was heated, stirred, and then dehydrated, to make 71.0 parts of the above-mentioned white powdery imidedicarboxylic acid disodium salt.

71 Parts of said imidedicarboxylic acid disodium salt was taken into 210 parts of dimethyl formamide, and after having added 0.7 parts of potassium iodide as a catalyst, 46.0 parts of allylchloride was added thereto over a period of 0.5 hour by heating at 150°C, and the reaction was further continued for 4.5 hours with refluxing.

After the reaction has finished, the precipiate was separated by filtration, excess of allylchloride and dimethyl formamide were removed under reduced pressure, and after having washed sufficiently with water, the organic layer was extracted with ether. By separating the organic layer and then removing the ether, a white powder was obtained. And by recrystallizing the so obtained white powder using the methanol, 70 parts of white needle-like crystals were obtained, having a melting point, 128° C. Infrared spectrum showed the imidering absorption at 1770 cm$^{-1}$, characteristic absorption of ester bond at 1710 cm$^{-1}$, and characteristic absorption of double bond at 926 cm$^{-1}$.

Elementary analysis has shown;
 Measured — C 67.41%, H 4.30%, N 3.49%
 Calculated — C 67.51%, H 4.38%, N 3.58%
 Iodine value, 129.0 (calculated, 129.7)

From the above results, it was confirmed that the product obtained is diallyl ester represented by the above formula (I-a).

ii. Synthesis of the same diallyl ester as those of above formula (I-a) by the method other than the above (i):

62.2 Parts of a 4-hydroxycarbonyl-N-(4-hydroxycarbonylphenyl)phthalimide and 21.8 parts of sodium carbonate were mixed and crushed, and introduced into an autoclave, and after having added thereto 46 parts of allylchloride and 2.0 parts of triethylamine, the mixture was reacted at 170° C for 7 hours with stirring. After the reaction has finished, the content was taken out, poured into acetone, and the insoluble parts were separated by filtration. After removing excess of allylchloride and acetone from the filtrate, the separated solid product was recrystallized using methanol to obtain 55.7 parts of white needle-like crystals having a melting point, 128° C. The crystals showed the same infrared spectrum as that obtained by the above method (i).

Elementary analysis has shown;
Measured — C 67.48%, H 4.41%, N 3.51%
Calculated — C 67.51%, H 4.38%, N 3.58%
Iodine value, 128.5 (calculated, 129.7)

Mixed examination with the diallyl ester obtained by the above method (i) has shown no drop in melting point.

The point analytical results have proved the product obtained to a diallyl ester represented by the above formula (I-a).

I-b Synthesis of 4-allyloxycarbonyl-N-(allyloxycarbonyl methyl)phthalimide of the above mentioned formula No. 1 i. 58.6 Parts of disodium salt of a 4-hydroxycarbonylN-(hydroxycarbonyl methyl)phthalimide of the formula

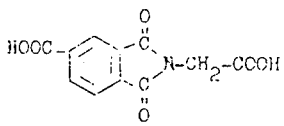

was taken into 176 parts of dimethyl sulfoxide, 0.10 part of triethylamine was added as a catalyst thereto, and 60 parts of allyl bromide was added thereto over a period of 0.5 hour by heating at 160°C, to further continue the reaction for 3.5 hours. After the reaction has finished, the sodium bromide formed as a by-product was separated by filtration and excess of allyl bromide was removed; then a large amount of water was added thereto and extraction of organic layer was repeated with ether. By removing the ether from the ether solution by heating under reduced pressure, and by recrystallizing the so obtained viscous liquid from the methanol, 60.3 parts of white needle-like crystals were yielded, m.p. 51°C. The infrared spectrum has shown a specific absorpion of ester at 1740 cm$^{-1}$ and 1710 cm$^{-1}$, absorption of double bond at 1640 cm$^{-1}$, and absortion of allyl group at 920 cm$^{-1}$ and 960 cm$^{-1}$.

Elementary analysis has shown;
Measured - C 62.57%, H 4.62%, N 4.14%
Calculated - C 62.00%, H 4.59%, N 4.25%
Iodine value, 155.0 (calculated, 154.1)

Furthermore, according to the NMR spectrum (solvent, trifluoroacetic acid) of the aove crystals, the peaks corresponding to each proton of the double bond —CH=CH—(—CH—CH$_2$—) of allyl group have the center value at 6.1 ppm (multiplet), 5.5 ppm (quartet), and 4.9 ppm (doublet.)

From the above analytical results, it was confirmed that the product obtained is a diallylester represented by the above formula (I-b).

ii. Synthesis of diallyester represented by the above formula (I-c) by the method other than the above (i):

58.6 Parts of disodium salt of a 4hydroxy carbonylN-hydroxycarbonyl methyl)phthalmide of formula

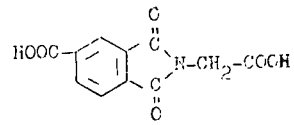

was taken into 290 parts of diethylene flycol monomethylether, and after having added 2 parts of triethylamine as a catalyst, 60 parts of allyl bromide was added thereto dropwise by heating at 180° C over a period of 1.0 hour, to continue the reaction for 5.0 hours with stirring and refluxing. After the reaction was finished, the insoluble parts were separated by filtration and excess of allyl bromide and diethylene glycol monomethyl ether were removed by heating under reduced pressure. By washing the so obtained viscous liquid with large amounts of water, and extracting the organic layer with ether to recrystallize it using the methano, 51.6 parts of white needlelike crystals were obtained, m.p. 51.5° C. The infrared absorption spectrum has shown the same characteristic absorption so that obtained by the above method (i).

Elementary analysis has shown;
Measured — C 62.51%, H 4.55%, N 4.28%
Calculated — C 62.60%, H 4.59%, N 4.25%
Iodine value, 154.7 (calculated, 154.2)

From the above analytical results, it was confirmed that the product obtained is a diallyl ester represented by the above formula (I-b).

iii. Synthesis of dially ester represented by the above formula (I-b) by the method other than the above (i) or (ii):

49.8 Parts of a 4-hydroxycarbonyl-N-(hydroxycarbonyl methyl)phthalimide, 1.35 parts of benzyldimethylamine, 60 parts of potassium carbonate, and 306 parts of allylchloride were fed into the pressure reaction vessel, and reacted at 150° C for 6.0 hours. After the reaction has finished, the content was taken out and the insoluble parts were separated by filtration as an acetone solution. After excess of allylchloride and acetone in the filtrate were removed under reduced pressure by heating, a large amount of water was added thereto to wash it sufficiently, and then the organic layer was extracted with ether. Recrystallization using methanol yielded 46.1 parts of white needle-like crystals, m.p. 51° C. The infrared spectrum has shown the same characteristic absorption as that obtained by the method (i) above.

Elementary analysis has shown;
Measured — C 62.59%, H 4.60%, N 4.21%
Calculated — C 62.60%, H 4.59%, N 4.25%
Iodine value, 154.3 (calculated 154.2)

I-c Synthesis of 4-allyloxycarbonyl-N-(3-allyloxycarbonylphenyl)phthalimide of the above mentioned formula No. 6.

62.2 Parts of a 4-hydroxycarbonyl-N-(3-hydroxycarbonylphenyl)phthalimide of the formula

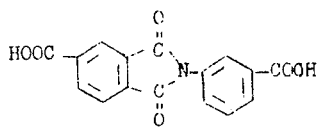

was dissolved into an aqueous solution containing 16.2 parts of sodium hydroxide in a homogeneous solution, and the solution was dehydrated to prepare 71.1 parts of the abovementioned white powdery imidedicarboxylic acid disodium salt.

7.1 Parts of said imidedicarboxylic acid disodium salt was taken into 210 parts of dimethyl formamide, 0.7 Part of potassium iodide was added thereto, and 50 parts of allylchloride was also added thereto dropwise at 150° C over a period of 0.5 hour, to continue the reaction of 5.0 hours with refluxing.

After the reaction has finished, the solid product precipitated was separated by filtration, and excess of allyl chloride and dimethyl formamide were removed from the filtrate under reduced pressure. And after adding a large amount of water to wash it sufficiently the organic layer was extracted with ether. By separating the organic layer and removing the ether therefrom, a white powder was obtained. By recrystallizing from methanol, 62 parts of a white diallyl ester was obtained, m.p. 115.0° C.

The infrared spectrum has shown the absorption of imide ring at 1770 cm$^{-1}$, characteristic absorption of ester bond at 1720 cm$^{-1}$, and characteristic absorption of allyl group at 1645 cm$^{-1}$.

Elementary analysis has shown;
Measured — C 67.45%, H 4.41%, N 3.52%
Calculated — C 67.51%, H 4.38%, N 3.58%
Iodine value, 129.0 (calculated 129.7)

The above results have proved the product obtained to be a diallyl ester represented by the above formula (I-c).

I-d Synthesis of 1,2-ethylene-bis(4-allyloxycarbonylphthalimide) of the above mention formula No. 7

59.6 Parts of anhydrous trimellitic acid and 9.0 parts of ethylene diamine were dissolved in 120 parts of dimethyl formamide, and 100 parts of m-xylene was also added thereby removing the forming water out of the system, to continue the reaction of 3.0 hours maintaining the temperature at 160° – 180° C.

After the reaction has finished, a large excess of water was added to obtain a faint yellowish precipitation. The precipitate was separated by filtration and washed sufficiently using hot water. After drying, 116 parts of 1,2-ethylene-bis(4-hydroxycarbonylphthalimide) of the formula

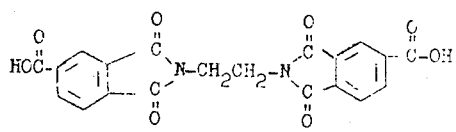

was obtained.

The so obtained 1,2-ethylene-bis(4-hydroxycarbonylphthalimide) was dissolved in an equivalent amount of sodium hydroxide aqueous solution. By removing the water, said diimidedicarboxylic acid disodium salt was obtained.

45.2 Parts of disodium salt of the so obtained 1,2-ethylene-bis(4-hydroxycarbonylphthalimide) was mixed into 136 parts of dimethylformamide, and by adding 0.4 part of triethylamide thereto as a catalyst, and maintaining the temperature at 140° C, 26.8 parts of allylchloride was added slowly and dropwisely thereto over a period of 0.5 hour. After the reaction for 3.5 hours, the reaction product was cooled, and the formed sodium chloride was separated by filtration. And by adding large amount of water to the filtrate, a white precipitate was formed. After washed sufficiently with water, the white precipitate was heated and dissolved into a mixed solvent of acetone: ethanol=3:1, and then cooled and recrystallized. The resulting crystals showed a melting point at 145° C. The infrared spectrum has shown the absorption of imide ring at 1770 cm$^{-1}$, ester bond absorption at 1720 cm$^{-1}$, and absorption of double bond at 1645 cm$^{-1}$.

Elementary analysis has shown;
Measured — C 63.98%, H 4.15%, N 5.70%
Calculated — C 63.93%, H 4.13%, N 5.74%
Iodine value, 103.2 (calculated, 103.9)

From the above analytical results, it was confirmed that the product obtained is a 1,2-ethylene-bis(4-allyloxycarbonylphthalimide) represented by the above formula (I-d).

I-e Synthesis of 1,6-hexamethylene-bis(4-allyloxycarbonylphthalimide) of the above mentioned formula No. 8.

i. 50.8 Parts of disodium salt of a 1,6-hexamethylenebis(4-hydroxycarbonylphthalimide) of the formula

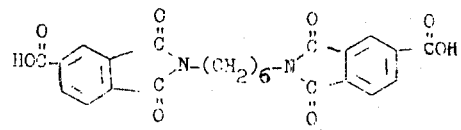

was dispersed in 100 parts of dimethyl sulfoxide, and by maintaining the external temperature at 160° C and allowing refluxing, 36.3 parts of allyl bromide was added thereto over a period of 1.0 hour. The reaction was continued for 2.0 hours in the same manner as the above method (I-d), and 46.2 parts of white crystals were obtained, melting at 116° C. The infrared spectrum has shown the imide-ring absorption at 1770 cm$^{-1}$, ester bond absorption at 1720 cm$^{-1}$, and double bond absorption at 1645 cm$^{-1}$.

Elementary analysis has shown;
Measured — C 66.20%, H 5.15%, N 5.09%
Calculated — C 66.17%, H 5.18%, N 5.14%
Iodine value, 93.1 (calculated 93.2)

The above analytical results have proved the product to be a 1,6-hexamethylene-bis(4-allyloxycarbonylphthalimide) of the above formula (I-e).

(ii) Synthesis of the same diallyl esters as those of above formula (I-e) by the method other than the above method (i):

46.4 Parts of a 1,6-hexamethylene-bis(4-hydroxycarbonylphthalimide) and 290 parts of allyl alcohol were introduced into a flask with refining tower, followed by the addition of 3.0 parts of sulfuric acid and 70 parts of m-xylene, and removing the water out of the reaction system, the reaction was carried out for 9.0 hours with refluxing. After the reaction has finished, an excess of allyl alcohol and m-xylene were removed under reduced pressure, and then by adding large amounts of water, the precipitate was filtered and repeatedly washed with an aqueous solution containing 10% by weight of sodium carbonate. The crude product obtained was recrystallized with a mixed solvent of acetone:methanol=1:3, and 35.4 parts of a white powder, m.p. 115° C. was obtained.

Elementary analysis has shown;
Measured — C 66.14%, H 5.21%, N 5.14%
Calculated — C 66.17%, H 5.18%, N 5.14%
Iodine value, 92.5 (calculated, 93.2)

The above analytical results have proved the product obtained to be a 1,6-hexamethylene-bis(4-allyloxycarbonylphthalimide) of the above formula (I-e).

(iii) Synthesis of the same diallyl esters as those of above formula (I-e) by the method other than the above (i) or (ii):

50.8 Parts of a 1,6-hexamethylene-bis(4-hydroxycarbonylphthalimide) disodium salt, 153 parts of allyl chloride, and 5.1 parts of triethylamine were fed to the stainless steel pressure reaction vessel, and the reaction was continued for 6.0 hours maintaining the external temperature a 170° C. After the reaction has finished, the content was eluted out with acetone, and the sodium chloride formed as a by-product was separted by filtration. Recrystallization in the same manner as the above (I-d) yielded 31.6 parts of a white powder, melting at 116° C. The infrared spectrum showed the same results as those of above (i) and (ii).

Elementary analysis has shown;
Measured — C 66.11%, H 5.22%, N 5.10%
Calculated — C 66.17%, H 5.18%, N 5.14%
Iodine value, 92.5 (calculated 93.2)

From the foregoing analysis, it was confirmed that the product obtained is a 1,6-hexamethylene-bis(4-allyloxycarbonylphthalimide) represented by the above formula (I-e).

I-f synthesis of 1,12-dodecamethylene-bis(4-allyloxycarbonylphthalimide) of the above mentioned formula No. 9

(i) 54.8 Parts of a 1,12-dodecamethylene-bis(4-hydroxycarbonylphthalimide) of the formula

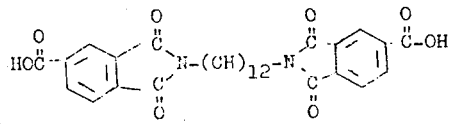

23.3 parts of sodium carbonate, and 0.9 part of benzyl trimethylammonium chloride were taken into 164 parts of dimethyl formamide, mixed heated sufficiently, and dissolved therein, and then by maintaining the external temperature at 160° C, 18.1 parts of allyl chloride was added dropwise thereto over a period of 1.0 hour. The reaction was continued for 3.0 hours in the same manner as in (I-d) above, and 54.7 parts of a white powder melting at 88° C was obtained.

The infrared spectrum has shown the imide absorption at 1770 cm$^{-1}$, absorption of carbonyl group of ester bond at 1710 – 1720 cm$^{-1}$, and absorption of double bond of allyl at 1640 cm$^{-1}$.

Elementary analysis has shown;
Measured — C 68.78%, H 6.40%, N 4.39%
Calculated — C 68.77%, H 6.41%, N 4.46%
Iodine value 80.4 (calculated, 80.7)

From the above analytical results, it was confirmed that the product obtained is a 1,12-dodecamethylene-bis(4-allyloxycarbonylphthalimide) represented by the above formula (I-f).

ii. Synthesis of the same diallyl esters as those of above formula (I-f) by the method other than that in above (i):

54.8 Parts of a 1,12-dodecamethylene-bis(4-hydroxycarbonylphthalimide) was introduced into a flask followed by the dropwise addition of 119 parts of thionyl chloride, and heated with refluxing. After the hydrochloric acid and sulfurous acid gases have stopped to evolve, tthe tionyl chloride was removed under reduced pressure. Extraction with ether gave 35.1 parts of a 1,12-dodecamethylene-bis(4-chlorocarbonylphthalimide).

58.5 parts of said imidecarboxylic acid chloride obtained by the above method and 145 parts of allyl alcohol were introduced into a flask equipped with a refluxing device and stirrer, and after adding 31.6 parts of pyridine as a hydrogen chloride capturing agent, the reaction was carried out for 7.0 hours with refluxing. After the reaction has finished, allyl alcohol and pyridine were removed under reduced pressure, and large amounts of water was added to obtain a white precipitation. By performing the treatment in the same manner as mentioned in (I-d) above, 33.3 parts of a white powder was obtained, m.p. 89° C.

The infrared spectrum has shown the same results as that of above (i).

Elementary analysis has shown;
Measured — C 68.70%, H 6.35%, N 4.48%
Calculated — C 68.77%, H 6.41%, N 4.46%
Iodine value, 80.1 (calculated, 80.7)

From the above analytical results, it was confirmed that the product obtained is a 1,12-dodecamethylene-bis(4-allyloxycarbonylphthalimide) represented by the above formula (I-f).

I-g Synthesis of metaphenylene-bis(4-allyloxycarbonylphthalimide) of the above mentioned formula No. 12

22.6 Parts of sodium salt of metaphenylene-bis(4-hydroxycarbonylphthalimide) was dispersed in 150 parts of dimethyl formamide, followed by the addition of 0.06 part of a potassium iodide. The mixture was introduced into an oil bath heated at 135° C, and when the inner temperature has reached 110° C, 15 parts of allyl chloride was added thereto dropwise over a period of 12 minutes. The mixture in an oil bath heated at 135° C was stirred and reacted for 4 hours. After the reaction has finished, the reaction mixture was introduced into the two times amount of water. The formed precipitate wa separated by filtration, washed with a caustic soda aqueous solution, and then washed sufficiently with water. The crystals obtained were recrystallized with cellosolve; resulting product showed m.p. 179° C. The infrared spectrum has shown the carbonyl group absorption of imide bond and ester bond at 1770 cm$^{-1}$ and 1720 cm$^{-1}$ respectively, and allyl group double bond absorption at 1640 cm$^{-1}$ and 920 cm$^{-1}$.

Elementary analysis has shown;
Measured — C 67.11%, H 3.79%, N 5.19%
Calculated — C 67.16%, H 3.76%, N 5.22%
Iodine value, 93.5 (calculated, 94.6)

From the above analytical results it was confirmed that the product obtained is a metaphenylene-bis(4- allyloxycarbonylphthalimide) represented by the above formula (I-g).

I-h Synthesis of 4,4'-dicyclohexylmethane-bis(4-allyloxycarbonylphthalimide) of the above mentioned formula No. 11

63.4 Parts of a 4,4'-dicyclohexylmethane-bis(4-hydroxycarbonylphthalimide) dipotassium salt was added to 317 parts of diethylene glycol monomethyl ether, followed by the addition of 6.3 parts of potassium iodide as a catalyst. And by maintaining the external temperature at 160° C, 115 parts of allyl chloride was added thereto dropwise over a period of 0.5 hour, to carry out the reaction for 4.0 hours with refluxing. After the reaction has finished, treatment was effected in the same manner as in (I-d) above, and 43.1 parts of a white powdery substance was obtained, m.p. 171° C. The infrared absorption spectrum has shown the carbonyl group absorption of imide bond and ester bond at 1770 $cm^{-1}$ and 1720 $cm^{-1}$.

Elementary analysis has shown;
Measured — C 69.61%, H 6.10%, N 4.33%
Calculated — C 69.58% H 6.00%, N 4.39%
Iodine value, 78.9 (calculated, 79.5)

From the above analytical results, it was confirmed that the product obtained is a 4,4'-dicyclohexylmethane-bis (4-allyloxyphthalimide) represented by the above formula (I-h).

I-i Synthesis of 4,4'-diphenylsulfoxide-bis(4-allyloxycarbonylphthalimide) of the above mentioned formula No. 14.

64.0 Parts of 4,4'-diphenylsulfoxide-bis(4-hydorxycarbonylphthalimide) disodium salt was added to 190 parts of N-methylpyrolidone followed by the addition of 19 parts of allyl fluoride over a period of 0.5 hour maintaining the external temperature at 140° C. The reaction product was treated in the same manner as in (I-d) above, and 47.6 parts of a faintly yellowish white powder was obtained, m.p. 163° C. The infrared absorption spectrum has shown the absorption of imide bond and ester bond at 1780 $cm^{-1}$ and 1720 - 1730 $cm^{-1}$ respectively, and absorption of double bond of allyl group at 920 $cm^{-1}$ and 940 $cm^{-1}$.

Elementary analysis has shown;
Measured — C 63.87%, H 3.61%, N 4.09%, S 4.80%
Calculated — C 63.90%m H 3.58%, N 4.14%, S 4.74%
Iodine value, 74.6 (calculated, 75.0)

From the above analytical results, it was confirmed that the product obtained is a 4,4'-diphenylsulfoxide-bis(4-allyloxycarbonylphthalimide) represented by the above formula (I-i).

I-j Synthesis of 4,4'-diphenylether-bis(4-allyloxycarbonylphthalimide) of the above mentioned formula No. 15.

13.8 Parts of disodium salt of a 4,4'-diphenylether-bis(4-hydroxycarbonylphthalimide) was dispersed in 100 parts of dimethyl formamide, followed by the addition of 0.04 part of potassium iodide. The mixture was introduced into an oil bath heated at 135° C, and when the inner temperature has reached 110° C, 8 parts of allylchloride was added thereto with stirring over a period of 5 minutes. Then by stirring the oil bath heated at 135° C, the reaction was continued for 4 hours. After the reaction has been completed, the reaction mixture was introuced to the two times amount of water. The precipitate formed was separated by filtration, washed with a caustic soda aqueous solution, and washed sufficiently with water. The crystals obtained were recrystallized with methyl cellosolve, and a white powder melting at 219° C was obtained. The infrared absorption spectrum has shown the absorption of imide bond and ester bond at 1775 $cm^{-1}$ and 1720 $cm^{-1}$ respectively, and absorption of double bond of allyl group at 1645 $cm^{-1}$.

Elementary analysis has shown;
Measured — C 68.72%, H 3.80%, N 4.38%
Calculated — C 68.78%, H 3.85%, N 4.46%
Iodine value, 79.9 (calculated, 80.8)

From the above analytical results, it was confirmed that the product obtained is a 4,4'-diphenylether-bis(4-allyloxycarbonylphthalimide) represented by the above formula (I-j).

I-k Synthesis of N,N'-bis(allyloxycarbonylmethyl) pyromellitdiimide of the above mentioned formula No. 17.

33.2 Parts of a N,N'-bis(carboxymethyl)pyromellitdiimide was neutralized in 8.0 parts of an aqueous solution containing sodium hydroxide with vigorous stirring, and then concentrated and dehydrated to obtain the above-mentioned white powdery disodium salt of imidedicarboxylic acid. 37.6 parts of said imidedicarboxylic acid disodium salt was dispersed in 300 parts of N,N-dimethylformamide, followed by the addition of 0.15 part of potassium iodide. The mixture was then intoduced into an oil bath heated at 150° C with stirring, and 23.1 parts of allyl chloride was then added thereto dropwise over a period of 0.5 hour. The oil bath was then heated for another 6 hours, cooled, and then the precipitated crystals were separated by filtration. The filtrate was poured into 800 parts of water, and the formed white precipitate was washed with an aqueous solution of 0.5% sodium hydroxide and then washed sufficiently with water. By recrystallizing the product with a mixed solvent of N,N-dimethylformamide and ethanol, 29.4 parts of white powdery crystals were obtained, m.p. 147° C. The infrared spectrum has shown the absorption of carbonyl group of imide bond and ester bond at 1770 $cm^{-1}$ and 1720 $cm^{-1}$ and absorption of allyl group double bond at 1640 - 1645 $cm^{-1}$.

Elementary analysis has shown;
Measured — C 58.20%, H 3.95% N 6.68%
Calculated — C 58.25%, H 3.91%, N 6.79%
Iodine value, 122.0 (calculated, 123.1)

The above results have proved the product obtained to be a diallyl ester represented by the above formula (I-k).

I-l Synthesis of N,N'-bis(3-allyloxycarbonylphenyl) pyromellitdiimide represented by the above mentioned formula No. 21.

50 Parts of disodium salt of a N,N'-bis(3-carboxyphenyl)pyromellitdiimide was dispersed in 300 parts of N,N-dimethylformamide containing 0.5 part of potassium iodide. The mixture was then introduced into an oil bath heated at 150° C with stirring, and 30.6 parts of allyl chloride was added dropwise thereto over a period of 0.5 hour. The oil bath was then heated at the same temperature and reacted for 6.0 hours, cooled, and the precipitate was separated by filtration. The filtrate was then poured into 1000 parts of water, and a brownish white precipitate was obtained. The precipitate was then recrystallized with a mixed solvent of N,N-dimethyl formamide and ethanol, and faintly yellowish white crystals were obtained. The infrared spectrum has shown the absorption of carbonyl group of imide bond and ester bond at 1775 $cm^{-1}$ and 1725 $cm^{-1}$ respectively and absorption of allyl group double bond at 1640 cm$^{-1}$, 985 cm$^{-1}$, and 910 cm$^{-1}$.

Elementary analysis has shown;
Measured — C 67.08%, H 3.72%, N 5.14%
Calculated — C 67.16%, H 3.76%, N 5.22%
Iodine value, 93.8 (calculated, 94.6)

From the above results, it was confirmed that the product obtained is a diallyl ester represented by the above formula (I-1).

I-m Synthesis of N,N'-bis(3-allyloxycarbonyl-cis-cyclohexyl)pyromellitdiimide represented by the above mentioned formula No. 19.

10.6 Parts of said imidedicarboxylic acid disodium salt obtained by neutralizing N,N'-bis(3-carboxy-cis-cyclohexyl)pyromellitdiimide with the sodium hydroxide and dehydrating it, was dispersed in 100 parts of an N,N-dimethylformamide containing 0.04 part of potassium iodide. The mixture was introduced into an oil bath heated at 130°– 140° C with stirring, and 7.0 parts of allyl chloride was added thereto dropwise over a period of 15 minutes. The oil bath was then maintained at the same temperature, reacted for 4.0 hours, cooled, and the precipitate was separated by filtration. The filtrate obtained was poured into 250 parts of water to cause precipitation, and the precipitate was washed with an aqueous solution of 0.1% sodium hydroxide, and then washed sufficiently with water. Recrystallization was effected using a mixed solvent of ethanol and toluene, and 7.1 parts of white crystals were obtained, melting at 208° C. The infrared absorption spectrum showed the absorption of carbonyl group of imide bond and ester bond at 1770 cm$^{-1}$ and 1710 – 1720 cm$^{-1}$ respectively and the absorption of allyl group double bond at 1645 cm$^{-1}$, 985 cm$^{-1}$, and 915 cm$^{-1}$.

Elementary analysis has shown;
Measured — C 65.63%, H 5.82%, N 5.04%
Calculated — C 65.68%, H 5.88%, N 5.11%
Iodine value, 91.4 (calculated, 92.5).

From the above results, it was confirmed that the product obtained is a diallyl ester represented by the above formula (I-m).

I-n Synthesis of N,N'-bis(allyloxycarbonylmethyl)-3,3',4,4'-diphenylsulfone-tetracarbodiimide represented by the above mentioned formula No. 23.

A N,N'-bis(carboxymethyl)-3,3',4,4'-diphenylsulfone-tetracarbodiimide obtained by the reaction of a diphenyl sulfone-3,3',4,'-tetracarboxylic acid dianhydride with glycine was neutralized with sodium hydroxide, and dehydrated to obtain a disodium salt of said imidedicarboxylic acid. 9.2 Parts of the disodium salt was dispersed in 150 parts of N,N-dimethylformamide containing 0.07 part of potassium iodide. The mixture was stirred in an oil bath heated at 130° C, and 6.1 parts of allyl chloride was added dropwise thereto requiring 10 minutes. The reaction was continued for 5 hours at the same temperature and was then cooled. The precipitate was separated by filtration, and the filtrate was poured into 3000 parts of water. The precipitate being formed was taken out by filtration, washed sufficiently with water, dried, and then recrystallized using methyl cellosolve to obtain crystals, m.p. 227° C. The infrared spectrum showed the absorption of imide bond and ester bond at 1775 cm$^{-1}$ and 1730 cm$^{-1}$ respectively, and the absorption of allyl group double bond at 1645 cm$^{-1}$ and 920 cm$^{-1}$.

The elementary analysis has shown;
Measured — C 56.48%, H 3.62%, N 5.01%, S 5.69%
Calculated — C 56.52%, H 3.65%, N 5.07%, S 5.80%
Iodine value, 92.1 (calculated 9.19)

From the above results, it was confirmed that the product obtained is a diallyl ester represented by the above formula (I-n).

I-o Synthesis of N,N'-bis(allyloxycarbonylpentamethyl)-3,3',4,4'-diphenylsulfone tetracarbodiimide of the above mentioned formula No. 24

A N,N'-bis(carboxypentamethyl)-3,3',4,4'-diphenylsulfone tetracarbodiimide obtained by the reaction of a diphenyl sulfone-3,3',4,4'-tetracarboxylic acid dianhydride with the caproic acid was neutralized with the sodium hydroxide to obtain a disodium salt. 10.1 parts of the disodium salt was dispersed in 150 parts of N,N-dimethylformamide containing 0.07 part of potassium iodide. After the mixture was introduced into a bath heated at 130° C with stirring, 6.1 parts of allyl chloride was added dropwise thereto, followed by the heating to maintain the same temperature for 7.5 hours. The bath was cooled, and the precipitate was separated by filtration. The filtrate was then poured into 3000 parts of water, and the precipitate being separated was recovered by centrifugal precipitation method. Recrystallization was effected by using methanol, followed by active carbon decolorization as an acetone solution, and recrystallization was effected again by using methanol. The crystals showed a melting point at 87° C. The infrared spectrum showed the absorption of imide bond and ester bond at 1775 cm$^{-1}$ and 1715 cm$^{-1}$ respectively and absorption of allyl group double bond at 1645 cm$^{-1}$ and 920 cm$^{-1}$.

Elementary analysis has shown;
Measured — C 61.40%, H 5.48%, N 4.29%, S 4.74%
Calculated — C 61.43%, H 5.46%, H 4.21%, S 4.82%
Iodine value, 75.6 (calculated, 76.4)

From the above results, it was confirmed that the product obtained is a diallyl ester represented by the above formula (I-o).

I-p Synthesis of N,N'-bis(3'-allyloxycarbonylphenyl)3,3',4,4'-diphenylsulfone-tetracarbodiimide of the above mentioned formula No. 25

A N,N'-bis(3'-carboxyphenyl)-3,3',4,4'-diphenylsulfone-tetracarbodiimide obtained from a diphenyl sulfone-3,3',4,4'-tetracarboxylic acid dianhydride and m-aminobenzoic acid, was reacted with allyl chloride in the same way as the above method (I-o), and a faintly brownish white precipitate was obtained. By washing the precipitate sufficiently with water, and drying it, white powdery crystals were obtained, m.p., 179° C. The infrared spectrum showed the absorption of carbonyl group of imide bond and ester bond at 1770 cm$^{-1}$ and 1720 cm$^{-1}$ respectively, and the absorption of allyl group double bond at 1640 – 1645 cm$^{-1}$.

Elementary analysis has shown;
Measured — C 63.81%, H 3.51%, N 4.03%, S 4.69%
Calculated — C 63.90%m H 3.57%, N 4.14%, S 4.74%
Iodine value, 76.2 (calculated, 75.0)

From the above results was confirmed that the crystals obtained are identical to a diallyl ester represented by the above formula (I-p).

I-q Synthesis of N,N'-bis(allyloxycarbonylmethyl)1,4,5,8-naphthalene tetracarbodiimide of the above mentioned formula No. 27

28 Parts of an N,N'-bis(carboxymethyl)-1,4,5,8-naphthalene tetracarbodiimide was neutralized with an aqueous solution containing 5.9 parts of sodium hydroxide, dehydrated, and a disodium salt of said dicarboxylic acid was obtained. 25 Parts of the disodium salt was dispersed in 100 parts of N,N-dimethylformamide containing 0.7 part of potassium iodide with vigorous stirring at 110° C, and 35.9 parts of allyl chloride was added dropwise thereto over a period of 30 minutes. The mixture was kept heated at the same temperature for 4 hours and cooled. The precipitate was separated by filtration, and the remaining filtrate was poured into 1000 parts of water to cause precipitation, and the resulting precipitate was washed sufficiently with water and dried. By effecting recrystallization using ethyl cellosolve, 21 parts of crystals were obtained, m.p. 96.0° C. The infrared spectrum showed the absorption of imide bond at 1750 cm$^{-1}$ and 1660 cm$^{-1}$, absorption of ester bond at 1700 cm$^{-1}$, and absorption of allyl group at 905 cm$^{-1}$ and 970 cm$^{-1}$.

Elementary analysis has shown;
Measured — C 62.30%, H 3.98%, N 6.11%
Calculated — C 62.34%, H 3.92%, N 6.06%
Iodine value, 109.0 (calculated, 109.8)

From the above results was confirmed that the product obtained is a diallyl ester represented by the above formula (I-q).

I-r Synthesis of N,N'-bis(3-allyloxycarbonyl-cis-cyclohexyl)-1,4,5,8-naphthalene-tetracarbodiimide of the above mentioned formula No. 29

44.5 Parts of an N,N'-bis(3-carboxy-cis-cyclohexyl)-1,4,5,8-tetracarbodiimide of the formula

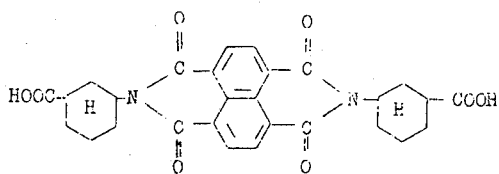

was added to an aqueous solution containing 6.9 parts of sodium hydroxide, with stirring being heated to a homogeneous solution, and dehydrated, to obtain 48.0 parts of a disodium salt of a white powdery imidedicarboxylic acid.

3.5 Parts of the disodium salt was taken into 120 parts of N,N-dimethylformamide, followed by the addition of 0.07 part of potassium iodide. The mixture was heated at 110° C, thereby dropwisely adding thereto 3.9 parts of allyl chloride over a period of 0.5 hour. The mixture was further heated and reacted for 4 hours, and cooled. The precipitated crystals were separated by filtration, an excess of allyl chloride and the solvent were removed from the filtrate under reduced pressure, and the residue was poured into 100 parts of water and washed sufficiently. The white crystals obtained by drying were recrystallized using ethyl cellosolve. The product showed a melting point at 250° C, and the infrared spectrum showed the absorption of 6-membered imide bond at 1735 cm$^{-1}$ and 1660 cm$^{-1}$, absorption of ester bond at 1710 cm$^{-1}$, and absorption of allyl group double bond at 910 cm$^{-1}$ and 990 cm$^{-1}$.

Elementary analysis has shown;
Measured — C 68.16%, H 5.77%, N 4.63%
Calculated — C 68.21%, H 5.73%, N 4.68%
Iodine value, 84.1 (calculated 84.8)

From the above results it was confirmed that the product obtained is a diallyl ester represented by the above formula (I-r).

Part II Synthesis of Prepolymer

II-a 100 Parts of diallyl ester represented by the above formula (I-a), 135 parts of benzoyl peroxide, and 100 parts of isopropyl alcohol were mixed together, and heated at a reflux temperature (82.5°–84.3° C) for 7 hours in an nitrogen atmosphere. The reaction mixture was cooled room temperature and then thrown into 250 parts of methanol which has been stirred violently and heated at 45° C.

The formed precipitate was washed and dried and dissolved in 30 parts of acetone. The solution was thrown again into 250 parts of methanol heated at 45° C. and stirred violently. The precipitate formed was washed sufficiently with methanol, and recovered by filtration. By drying it, a white powdery prepolymer was obtained in 24% yield; softening point, 101°–112° C, iodine value, 24, average molecular weight 5400. Relative viscosity of the prepolymer at 30° C was 1.21. Also the molecular weight per double bond in the prepolymer calculated from above iodine value was 1060.

II-b A mixture of 100 parts of diallyl ester represented by the above formula (I-b) and 0.11 part of lauroyl peroxide was stirred in an nitrogen atmosphere and heated from room temperature to 100° C over 1 hour, and reacted for 4.5 hours at 100 ± 1° C. The reaction was then cooled to 80° C and allowed to flow down in filament from into 350 parts of methanol with violent stirring. The formed precipitate was separated by filtration, and by adding 50 parts of new methanol thereto with violent stirring by heating at 50°–60° C, the product soluble in methanol was removed by extraction. And by separating and drying the formed precipitate, 28 parts of the aimed prepolymer was obtained. The prepolymer was a white powder having iodine value of 54 and average molecular weight of 6700. Relative viscosity of the repolymer at 30° C was 1.10. The molecular weight per double bond in the prepolymer calculated from the above iodine value was 470.

II-c 100 Parts of diallyl ester represented by the above formula (I-c), 2 parts of dicumyl peroxide, and 100 parts of xylene was mixed together, and the mixture was heated to 100°–140° C for 4 hours with stirring in an nitrogen atmosphere. The reaction mixture obtained was poured into a mixed solvent of 200 parts of acetone and 300 parts of methanol, and a prepolymer was obtained in 10% yield. The prepolymer showed iodine value of 48 and average molecular weight of 5800, and the relative viscosity in N,N-dimethylformamide was 1.12. The molecular weight per double bond in the prepolymer calculated from the above iodine value was 530.

II-d Polymerization was done by mixing 100 parts of diallyl ester of the above formula (I-d), 20 parts of carbon tetrachloride, and 1.1 parts of benzoyl peroxide and holding at a reflux temperature for 6.5 hours. The convertion of prepolymer was 23% with respect to the monomer fed. By stirring the reaction mixture at 50° C under reduced pressure of 18 mmHg, a carbon tetrachloride was recovered. To the reaction mixture was added 500 parts of methanol with violent stirring and the monomer was extracted therefrom by extraction; solid parts were recovered by filtration, washed and dried. The rate of optical density D(1645)/D(1600) of IR spectrum of the obtained white powderly prepolymer showed the presence of 30% of unsaturated double bond with respect to monomer and average molecular weight of 4600. Also the relative viscosity of the prepolymer was 1.08. The molecular weight per double bond in the prepolymer calculated from the above unsaturated bond concentration was 820.

II-e To the mixture consisting of 50 parts of diallyl ester represented by the above formula (I-e) and 50 parts of diallyl ester represented by the above formula (I-f) was added 0.09 part of benzoyl peroxide with sufficient stirring in an nitrogen atmosphere, and the mixture was heated from room temperature to 120° C over a period of 2 hours and held the reaction for 5 hours at 120 ± 1° C. The reaction mixture was then allowed to flow down in a filament form into 650 parts of methanol which has been stirred, and the formed precipitate was washed and dried to obtain 19 parts of white powdery prepolymer. The product showed iodine value, 37 and average molecular weight, 6300. Relative viscosity of the prepolymer was 1.09. The molecular weight per double bond in the prepolymer calculated from the above iodine value was 690.

II-f 100 Parts of diallyl ester represented by the above formula (I-h), 30 parts of cumene, and 2 parts of benzoyl peroxide were mixed together, and held at 100° C for 6 hours. The reaction mixture was then pumped into a colloid mill (clearance between rotor and stator being 0.001 in., 3600 rpm. works at a flow rate of 757 liters per hour.) together with about five times by volume of methanol. The mixture from the colloid mill was cooled to 5° C, recovered by filtration, washed with cool methanol, dried at room temperature under reduced pressure, to obtain a prepolymer. The ratio of optical density D(1645)/D(1600) of IR spectrum of the white powdery prepolymer showed the presence of 38% of unsaturated bond with respect to the monomer, and average molecular weight of 5700. Relative viscosity of the prepolymer was 1.11. Also, the molecular weight of double bond in the prepolymer was calculated from the above double bond concentration to be 820.

II-g 100 Parts of diallyl ester represented by the above formula (I-k), 100 parts of methylethyl ketone, and 2.3 parts of benzoyl peroxide were mixed together, heated at a reflux temperature for 7 hours.

Then the reaction mixture was allowed to flow slowly into about 500 parts of isopropanol which was heated at 60° C and stirred violently, and the solid part was recovered by filtration, washed and dried. The ratio of optical density D(1645)/D(1600) of IR spectrum of the white powdery prepolymer showed the presence of 29% of unsaturated bond with respect to the monomer, average molecular weight of 3200. The conversion was 18%. Relative viscosity of the prepolymer in N,N-dimethylformamide was 1.05, and the molecular weight per double bond in the prepolymer was calculated from the above unsaturated double bond concentration to be 710.

II-h A mixture composed of 80 parts of diallyl ester represented by the above formula (I-a), 20 parts of 2,6-diallyl naphthalate, one part of dicumyl peroxide, and 100 parts of xylene, was held at 100° – 140° C for 5 hours with stirring in an nitrogen atmosphere. The reaction mixture was then poured into 500 parts of methanol heated at 60° C, and a prepolymer was obtained (yield, 8%) as a white precipitate. The prepolymer was further dissolved in N,N-dimethylformamide and then poured into methanol, to effect reprecipitation, i.e., purification. The prepolymer showed an iodine value of 56 and an average molecular weight of 6200. Relative viscosity in N,N-dimethylformamide was 1.08. And the nitrogen analysis of the prepolymer showed the nitrogen content of 2.74%, indicating the constituting ratio of said prepolymer to be 77 to 23 in terms of mol ratio of diallyl ester unit represented by the above (I-a) to diallyl naphthalate unit. Also the molecular weight per double bond in the prepolymer was calculated from the above iodine value to be 450.

II-i In order to examine the preservation stability of the prepolymers prepared by the above-mentioned methods (II-a) through up to (II-g), each prepolymer was heat-treated for 20 hours in an air oven set at 100° C, so that change in flow properties before and after the treatment can be measured. For the purpose of comparison, flow properties of the diallylisophthalate prepolymer (average molecular weight, 11000 and iodine value, 63) were also measured. Results are shown in Table 1 below.

Table 1

| | Pre-polymer | Amount plunger has lowered down (mm/min) | | Flow property holding rate (%) |
| --- | --- | --- | --- | --- |
| | | Before heat treatment | After heat treatment at 100° C for 20 hours | |
| Example | II-a | 6.3 | 4.4 | 70 |
| | II-b | 5.9 | 3.9 | 66 |
| | II-c | 7.5 | 5.1 | 68 |
| | II-d | 11.3 | 9.6 | 85 |
| | II-e | 6.7 | 4.7 | 70 |
| | II-f | 8.2 | 4.3 | 52 |
| | II-g | 5.7 | 4.0 | 70 |
| | II-h | 8.5 | 6.8 | 80 |
| Comparative Example | DAI | 4.5 | 0.2 | 4 |

As will be apparent from Table 1 above, the prepolymers derived from the aromatic imidedicarboxylic acid diallyl esters of this invention, show very good preservation stability.

Part III Preparation of Hardened Resin

III-a 5 Parts of a 4-allyloxycarbonyl-N-(4'-allyloxycarbonylphenyl)phthalimide of the above formula (I-a), and 95 parts of the prepolymer of the above-mentioned diallyl ester prepared in (II-a) above were mixed well together with 100 parts of glass short fibers, CLASSRON CHOPPED STRAND CS-03 HB (Asahi Fiber Glass K.K.), 2 parts of cumene hydroperoxide, and 200 parts of acetone, and the mixture was air-dried and mixed by a pair of rollers heated at 100° C, to make a molding compound.

The so prepared molding compound was held in a mold heated at 180° C under a pressure of 450 Kg/cm² for 15 minutes, and a hardened resin was obtained.

For the purpose of comparison, hardened resins (Comparative Example 1 and Comparative Example 2) were also prepared in the same manner as the above method but by using a diallyl orthophthalate (hereinafter abbreviated as DAO) and a diallyl orthophthalate prepolymer (average molecular weight, 14000; iodine value, 55), and a diallyl isophthalate (hereinafter abbreviated as DAI) and a diallyl isophthalate prepolymer (average molecular weight, 11000; iodine value, 63), respectively, in place of using the above-mentioned dially ester (I-a) and prepolymer (II-a).

Mechanical properties, thermal properties, and electrical properties, of the hardened resins obtained above are listed below in Table 2.

Table 2

| Hardened resin | Example III-a | Comparative Example 1 | Comparative Example 2 |
| --- | --- | --- | --- |
|  | Diallyl ester (I-a) | DAO | DAI |
| Flexural strength (Kg/mm$^2$) | 7.1 | 8.2 | 6.0 |
| Flexural modulus (Kg/mm$^2$) | 650 | 790 | 700 |
| Heat distortion temperature (° C) | >270 | 180 | 250 |
| Temperature at which weight loss starts (° C) | 350 | 269 | 303 |
| Volume resistivity (ohms-cm) | 4 × 10$^{16}$ | 3 × 10$^{13}$ | 7 × 10$^{13}$ |
| Dielectric constant (at 1 KHz) | 3.0 | 4.6 | 4.5 |
| Dissipation factor (at 1 kHz) | 0.008 | 0.014 | 0.015 |
| Arc resistance (sec) | 180 | 130 | 140 |

As shown in Table 2 above, a hardened resin made from diallyl ester (I-a) of this invention provides superior electrical properties, thermal properties, and mechanical properties.

The hardened resins made from each of the above diallyl ester (I-a), DAO, and DAI were treated in an air oven heated at 260° C for 10 – 1000 hours, to measure the weight losses and flexural strength before and after the treatment. Results are shown in Table 3 below.

Table 3

| Hardened resin | | | Example III-a | Comparative Example 1 | Comparative Example 2 |
| --- | --- | --- | --- | --- | --- |
| | | | Diallyl ester (I-a) | DAO | DAI |
| | | Before treatment | 7.1 | 8.2 | 6.0 |
| Flexural strength (Kg/mm$^2$) | After treatment | 260° C × 10 hrs. | 7.4 | 1.6 | 4.8 |
| | | 260° C × 100 hrs. | 6.6 | 0 | 1.3 |
| | | 260° C × 1000 hrs. | 6.0 | (Measurement impossible) | 0.6 |
| | | 260° C × 10 hrs. | 0.2 | 17.5 | 1.6 |
| Weight loss (%) | | 260° × 100 hrs. | 0.8 | 33.0 | 18.8 |
| | | 260° C × 1000 hrs. | 1.9 | (Measurement impossible) | 29.1 |

As shown in Table 3 above, the resin of diallyl ester (I-a) reinforced with a glass fiber shows marked heatresistance.

Resistance to chemicals (Barcol hardness holding ratio (%) after being boiled for a determined period of time in the chemicals shown) of each of the above hardened resins are listed in Table 4 below.

Table 4

| Hardened resin | | Example III-a | Comparative Example 1 | Comparative Example 2 |
| --- | --- | --- | --- | --- |
| | | Diallyl ester (I-a) | DAO | DAI |
| 10% NaOH Aqueous solution | 50 hrs. | 93 | 83 | 87 |
| | 100 hrs. | 80 | 56 | 69 |
| 10% H$_2$SO$_4$ Aqueous solution | 50 hrs. | 94 | 88 | 90 |
| | 100 hrs. | 85 | 78 | 82 |

III-b - III-c 100 Parts of a 4-allyloxycarbonyl-N-(3'-allyloxycarbonylphenyl)phthalimide repesented by the above formula (I-c) and 2 parts of dicumyl peroxide were mixed together, heated and poured into a mold of parallel cubic form (125 mm × 75 mm × 6 mm), and heated from 100° C up to 180° C at a rate of 6° C per hour, to obtain a transparent hardened resin (III-b).

Quite in the same way as above, a hardened resin (III-c) was prepared from a dodecamethylene-bis(4-allyloxycarbonylphenylphthalimide) represented by the above formula (I-f).

Furthermore, for the purpose of comparision, transparent hardened resins (Comparative Examples 3 and 4) were obtained by carrying out the hardening reaction in the same manner as the above method but using DAO and DAI in place of the above-mentioned diallyl ester.

Properties of each of the hardened resins so obtained are shown in Table 5 below.

Table 5

| Hardened resin | Example III-b Diallyl ester (I-c) | Example III-c Diallyl ester (I-f) | Comparative Example 3 DAO | Comparative Example 4 DAI |
|---|---|---|---|---|
| Flexural strength (Kg/mm$^2$) | 6.2 | 9.8 | 8.0 | 5.0 |
| Flexural modulus (Kg/mm$^2$) | 300 | 160 | 320 | 230 |
| Heat distortion temperature (°C) | >250 | 260 | 150 | 220 |
| Temperaure at which weight loss starts (°C) | 345 | 330 | 276 | 303 |
| Heat deterioration test Weight loss (%) 260°C, 10 hrs. | 1.3 | 1.1 | 30 | 2.0 |
| 260°C, 100 hrs. | 4.0 | 5.2 | 52 | 32 |
| 260°C, 1000 hrs. | 5.2 | 9.6 | (Measurement impossible) | (Measurement impossible) |

As shown in Table 5, it was confirmed that the hardened resins obtained from the diallyl esters (I-c) and (I-f) of this invention possess very distinguished heatresistance.

III-d - III-g Hardened resins reinforced with a glass fiber were preparedby using the prepolymers II-b, II-e, II-f, and II-d in the same manner as in Example III-a, under the molding conditions shown in Table 6.

Heat deterioration test at 260° C of each of the so prepared hardened resins showed in the results as listed in Table 6. As will be apparent from the results, the harded resin prepared from the diallyl esters of this invention exhibits quite good resistance against heat.

Table 6

| | | Example III-d | Example III-e | Example III-f | Example III-g |
|---|---|---|---|---|---|
| Raw Material Composition | Prepolymer Amount | Prepolymer II-b 90 parts | Prepolymer II-e 90 parts | Prepolymer II-f 90 parts | Prepolymer II-d 90 parts |
| | Monomer Amount | Diallyl ester I-b 10 parts | Diallyl ester I-f 10 parts | Diallyl ester I-b 10 parts | Diallyl ester I-b 10 parts |
| | Initiator Amount | t-Butyl perbenzoate 2 parts | Dicumyl peroxide 2 parts | Cumene hydroperoxide 3 parts | Dicumyl peroxide 2 parts |
| | Amount of Glass short fiber | 100 parts | 100 parts | 100 parts | 100 parts |
| Molding Condition | Temperature (°C) | 170 | 170 | 190 | 180 |
| | Pressure (Kg/cm$^2$) | 750 | 750 | 750 | 750 |
| | Time (min.) | 15 | 15 | 15 | 15 |
| Before treatment | Flexural strength (Kg/mm$^2$) | 9.1 | 8.6 | 7.1 | 7.7 |
| 260°C - 10 hrs. After treatment | Flexural strength (Kg/mm$^2$) | 8.7 | 8.9 | 7.2 | 5.7 |
| | Weight loss (%) | 0.7 | 0.4 | 0.5 | 0.2 |
| 260°C - 100 hrs. After treatment | Flexural strength (Kg/mm$^2$) | 5.5 | 6.0 | 5.0 | 5.7 |
| | Weight loss (%) | 2.2 | 1.6 | 1.0 | 0.7 |
| 260°C - 1000 hrs. After treatment | Flexural strength (Kg/mm$^2$) | 3.2 | 4.1 | 4.3 | 5.4 |
| | Weight loss (%) | 9.9 | 5.8 | 4.2 | 2.2 |

III-h 92 Parts of the prepolymer of an N,N'-bis(allyloxycarbonylmethyl)pyromellitdiimide prepared in II-g above, 8 parts of diallylisophthalate, 2.2 parts of t-butyl perbenzoate, 0.022 part of hydroquinone, and 100 parts of glass short fiber were mixed together by a pair of mixing rollers heated at 90° – 110° C, and heated under the conditions of 175° C, 400 Kg/cm$^2$ for 16 minutes, to obtain a hardened resin.

The so obtained hardened resin showed quite excellent heat-resistance as shown in Table 7.

Table 7

| | Flexural strength (kg/cm$^2$) | Weight loss (%) |
|---|---|---|
| Before treatment | 79 | 0 |
| 260°C, 10 hrs. | 5.9 | 0.3 |

Table 7-continued

| | Flexural strength (kg/cm$^2$) | Weight loss (%) |
|---|---|---|
| After treatment 260°C, 100 hrs. After treatment | 5.5 | 1.0 |
| 260°C, 1000 hrs. After treatment | 5.0 | 2.7 |

III-i 90 Parts of precopolymer (molecular weight, 6300; iodine value, 37) of diallyl ester (I-e) and diallyl ester (I-f) prepared in II-e above, 10 parts of diallyl ester (I-f), 2 parts of a dicumyl peroxide, 100 parts of glass short fibr (same as that used in Example III-a), and 200 parts of methylethyl ketone, were mixed together. The mixture was air-dried and mixed by a pair of rollers heated at 100° C, and crushed to obtain a molding compound.

The so prepared molding compound was molded under the same conditions as those as those of Example III-a, and a hardened resin was obtained.

Properties of the hardened resin, and flexural strength, and rate of weight loss after being heat-treated under the same conditions as those of Example III-a are listed in Table 8 below.

Table 8

| | |
|---|---|
| Flexural strength (Kg/mm$^2$) | 8.6 |
| Flexural modulus (Kg/mm$^2$) | 590 |

Table 8-continued

| Heat distortion temperature (° C) | | | >270 |
|---|---|---|---|
| Treated at 260°C | Flexural strength (Kg/mm²) | After 10 hrs. | 8.9 |
| | | After 100 hrs. | 6.0 |
| | | After 1000 hrs. | 4.1 |
| | Weight loss (%) | After 10 hrs. | 0.4 |
| | | After 100 hrs. | 1.6 |
| | | After 1000 hrs. | 5.8 |

As will be apparent from Table 8 above the hardened resin obtained from the diallyl esters of this invention showed excellent mechanical and thermal properties.

III-j = III-m 80 Parts of a 4-allyloxycarbonyl-N-(4'-allyloxycarbonylphenyl)phthalimide represented by the above formula (I-a), 20 parts of 2,6-diallyl naphthalate (hereinafter abbreviated as DAN), and 2 parts of dicumyl peroxide were fed into the same cast mold as used in Example III-b, and heated from 100° C up to 180° C over a period of 4 hours, and after-cured by being held a 180° C for 2 hours, to obtain a hardened resin (III-j).

Hardened resins (III-k to III-m) were prepared in the same manner as in III-j above using the diallyl esters (I-a) and (I-f) of this invention in combination with DAN and DAI in amounts as shown in Table 9.

Weight loss on heating of the hardened resins obtained as mentioned above and of the hardened resins of DAO (Comparative Example 3) and DAI (Comparative Example 4) obtained in Example III-b for the purpose of comparison were examined. Results were as shown in Table 9.

Table 9

| | Hardened resin composition | | | Temperature at which 5% of weight is lost (° C) |
|---|---|---|---|---|
| | Diallyl ester of this invention (A) | Copolymeric monomer (B) | Weight ratio (A/B) | |
| Example III-j | I-a | DAN | 80/20 | 360 |
| Example III-k | I-a | DAN | 70/30 | 353 |
| Example III-l | I-a | DAI | 80/20 | 357 |
| Example III-m | I-f | DAN | 80/20 | 343 |
| Comparative Example 3 | — | DAO | 0/100 | 304 |
| Comparative Example 4 | — | DAI | 0/100 | 331 |

Table 9 above proves that the hardened resins obtained by using the diallyl esters of this invention in combination of a little amount of copolymeric monomer, show very good resistance to heat.

III-n III-q To 100 parts of diallyl ester monomer represented by the above formula (I-o) were added 2 parts of a dicumyl peroxide and 1 part of a cumenehydroperoxide as free radical initiators, and the mixture was casted and hardened in the same manner as in Example III-j above, to obtain a transparent hardened resin (Example III-n).

Quite in the same manner as in Example III-n above, the cast hardened resins were prepared from the mixture (III-o) of diallyl esters (I-b) and (I-n) at a weight basis ratio of 80 to 20, from the mixture (III-p) of diallyl esters (I-c) and (I-K) at a weight basis ratio of 70 to 30, and from the mixture (III-q) of diallyl esters (I-a) and (I-b) at a weight basis ratio of 50 to 50.

The temperature at which each of the above hardened resins showed 5% of weight loss as measured by thermal gravimetry, were as listed in Table 10 below, indicating good resistance to heat.

Table 10

| Example | Hardening resin composition (diallyl ester) | Temperature at which 5% of weight is lost (0° C) |
|---|---|---|
| III-n | I-o | 373 |
| III-o | I-b + I-n (80/20) | 355 |
| III-p | I-c + I-k (70/30) | 364 |
| III-q | I-a + I-b (50/50) | 335 |

What is claimed is:

1. A curable prepolymer in which (1) 100–60 mol% of the total recurring units consists of recurring units expressed by the following formula

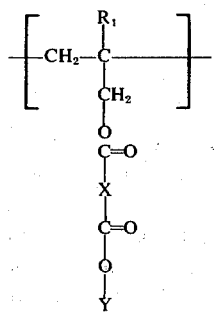

wherein Y is an allyl group of the formula

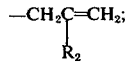

$R_1$ and $R_2$ are the same or different and represent a hydrogen atom or methyl group; and X is a trivalent or tetravalent aromatic radical expressed by the formula

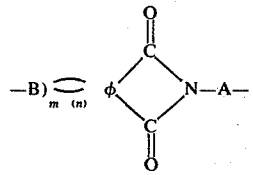

in which $\phi_1$ is

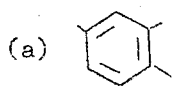 , 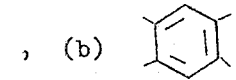 ,

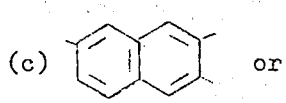 or 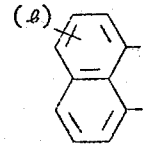

(e) showing an m- or p-oriented bond,

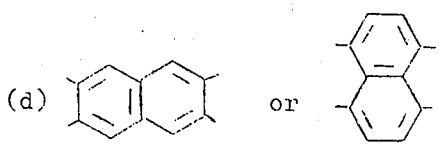

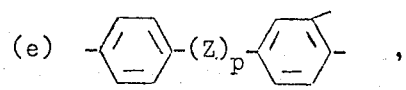

or

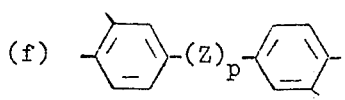

$p$ in the formulae (e) and (f) represents 0 or 1, when $p$ is 0, the two benzene rings are directly bonded, and when $p$ is 1, Z is $-SO_2-$, $-O-$ or a divalent lower hydrocarbon residue; m and n are 0 or 1, when one of $m$ and $n$ is 0, the other is also 0, and in this case the allyloxy carbonyl group expressed by the formula

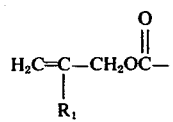

is directly bonded to $\phi_1$, and when n and m are both

represents the following formula

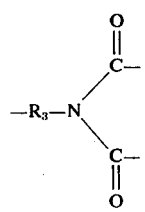

wherein $R_3$ is a divalent aliphatic, alicylic or aromatic organic radical, and A is an atomic group of the following formula

or

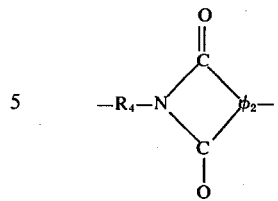

wherein $R_4$ is a divalent aliphatic, alicyclic or aromatic organic radical and are the same as or different from $R_3$, and $\phi 2$ is a trivalent aromatic radical of formula (a), (c) or (e) $\phi 2$ and $\phi 1$ being the same or different, with the proviso that X is bonded to

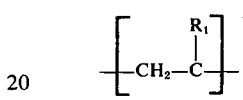

through

either via A or B, (2) and 0 - 40 mol % of the total recurring units consisting of recurring units expressed by the formula

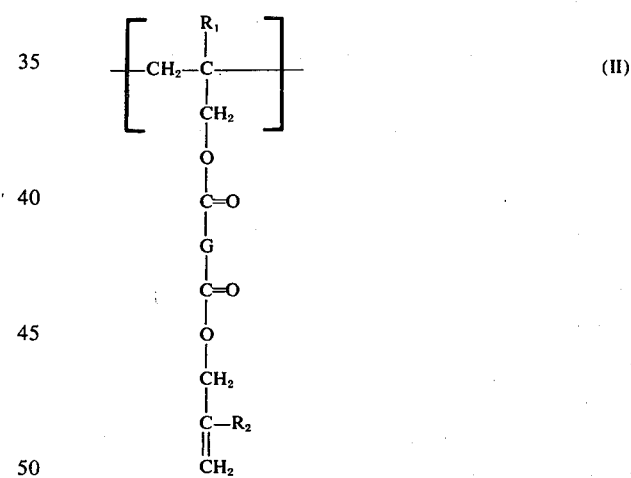

wheein $R_1$ and $R_2$ are the same or different and represent a hydrogen atom or methyl group, and G is a divalent aliphatic, alicyclic or aromatic hydrocarbon radical having 1 to 12 carbon atoms, said prepolymer having a relative viscosity ($\eta$rel.), as measured at 30° C. on a solution of 1.0g of the prepolymer in 100 ml. of N,N-dimethyl formamide as a reference solvent, of 1.05 to 1.25.

2. The prepolymer of claim 1 which has a molecular weight of not more than 800 on an average per double bond of allyl group contained therein.

3. A process for producing the curable prepolymer of claim 1 which comprises heating (1) 100 - 60 mol % of an aromaic imidodicarboxylic acid diallyl ester of the formula

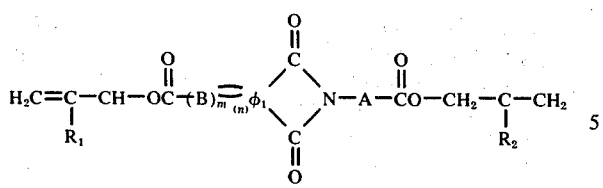

wherein $R_1$, $R_2$, 1, m, n, and A are the same as defined in claim 1, the total of the above (1) and (2) being 100 mol % in the presence of a free radical initiator to polymerize said diallyl ester, stopping the polymerization reaction before the polymeric reaction mixture is gelled, and separating and recovering the polymerized product.

4. A curable composition comprising
   at least a compound selected from the group consisting of a diallyl ester consisting of 100 – 60 mol % of an aromatic diimidodicarboxylic acid diallyl ester of the formula

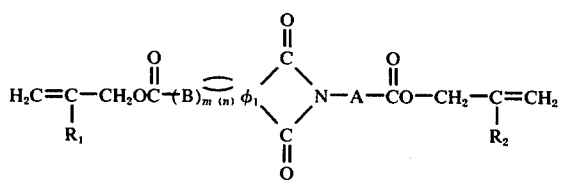

wherein $R_1$ and $R_2$ are the same or different and represent a hydrogen atom or methyl group; $\phi1$ is a trivalent or tetravalent aromatic group expressed by the following formula, (a) 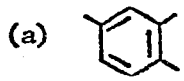, (b) 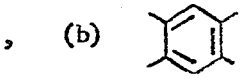

(c) 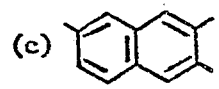 or 

(1) represents an m- or p-oriented bond, (d) 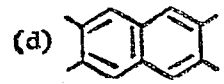 or 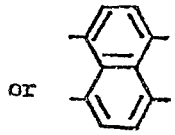

(e) 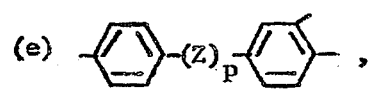, or, (f) 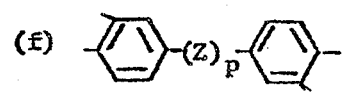

p in the formulae (e) and (f) representing 0 or 1, and when p is 0, the two benzene rings are directly bonded to each other, and when p is 1, z is —$SO_2$—, —O—, or a divalent lower hydrocarbon residue; m and n each represent 0 or 1, when one of m or n is 0, the other is also 0, and in this case, the allyloxy group of the formula

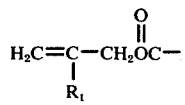

to $\phi1$, and when m and n are both 1,

represents the following formula

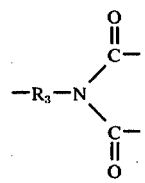

wherein $R_3$ is a divalent aliphatic, alicyclic, or aromatic organic radical; and A represents the following formula

—$R_4$— or

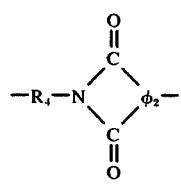

wherein $R_4$ is a divalent aliphaic, alicylic, or aromatic organic radical and is the same as or difference from $R_3$, and $\phi2$ represents a trivalent aromatic group (a), (c) or (e), $\phi2$ and $\phi1$ being the same or different, or 2. a curable prepolymer in which at least 60 mol% of the total structural units consists of recurring units of the following formula

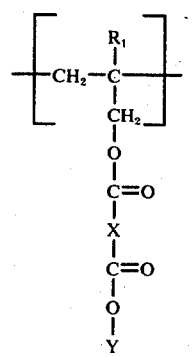

wherein $R_1$, X and Y are the same as defined in claim 1, and 0 –40 mol % of the total structural units consisting of the recurring units of the following formula

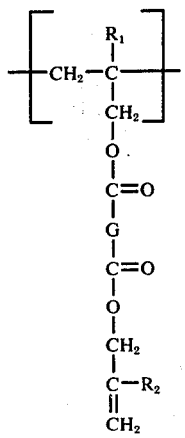

wherein $R_1$, $R_2$ and G are the same as defined in claim 1, said prepolymer having a relative viscosity, as measured in a solution of 1.0 g of the prepolymer in 100 ml. of N,N-dimethyl formamide as a reference solvent, of 1.05 to 1.25, or 3. a mixture of said diallyl ester (1) and said prepolymer (2), and
4. a free radical initiator of 0.03 to 5% by weight per 100 parts by weight of the above (1), (2) or (3),
5. A shaped article composed of the cured resin of claim 4.
6. The composition of claim 4 including at least one additive of the group consisting of copolymerizable unsaturated compounds, fillers, reinforcing materials, coloring agents, oxidizing agents and mold release agents.

* * * * *

UNITED STATES PATENT AND TRADEMARK OFFICE
CERTIFICATE OF CORRECTION

PATENT NO. : 3,991,040

DATED : November 9, 1976

INVENTOR(S) : Toshihiro Santa et al.

It is certified that error appears in the above-identified patent and that said Letters Patent are hereby corrected as shown below:

Claim 1, third formula (lines 46-52), delete in its entirety and insert the following therefor:

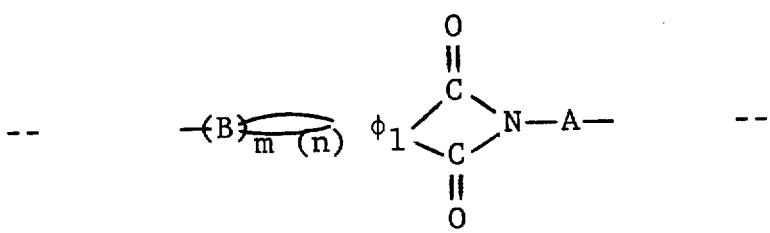

Claim 1, column 47, line 1, delete "(e)", insert -- ($\ell$) --

Claim 1, column 47, line 42, after "both" insert -- 1, --

Claim 1, column 47, line 46, delete the formula in its entirety and insert the following therefor:

Claim 1, column 48, lines 1-9, delete the formula in its entirety and insert the following therefor:

UNITED STATES PATENT AND TRADEMARK OFFICE
CERTIFICATE OF CORRECTION

PATENT NO. : 3,991,040

DATED : November 9, 1976

INVENTOR(S) : Toshihiro Santa et al.

It is certified that error appears in the above-identified patent and that said Letters Patent are hereby corrected as shown below:

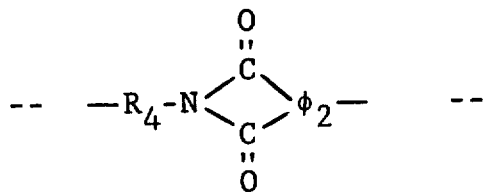

Claim 3, column 49, lines 1-8, delete the formula in its entirety and insert the following therefor:

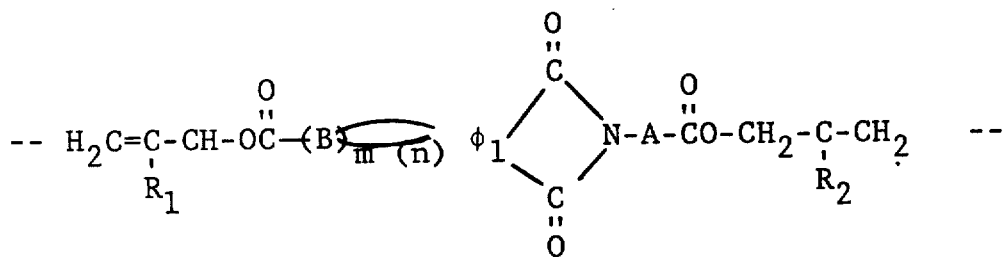

Claim 4, column 49, lines 23-30, delete the formula in its entirety and insert the following therefor:

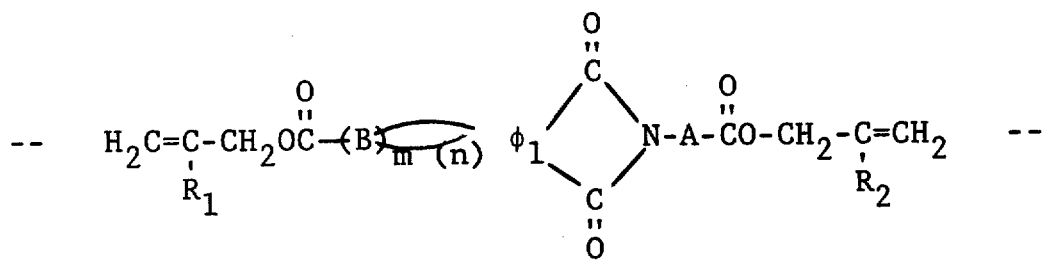

UNITED STATES PATENT AND TRADEMARK OFFICE
CERTIFICATE OF CORRECTION

PATENT NO. : 3,991,040
DATED : November 9, 1976
INVENTOR(S) : Toshihiro Santa et al.

It is certified that error appears in the above-identified patent and that said Letters Patent are hereby corrected as shown below:

Claim 4, column 50, lines 17-18, delete the formula in its entirety and insert the following therefor:

$$-- \;\; -(B)_{\overline{m}\;(n)} \;\; --$$

Claim 4, line 43 of column 50, delete "aliphaic", insert -- aliphatic --

Claim 4, column 52, line 8, delete "0.03", insert -- 0.3 --

Claim 4, column 52, line 9, delete "," in second instance, insert -- . --

Signed and Sealed this

Twenty-ninth Day of March 1977

[SEAL]

Attest:

RUTH C. MASON
Attesting Officer

C. MARSHALL DANN
Commissioner of Patents and Trademarks